United States Patent
Kim et al.

(10) Patent No.: US 9,530,973 B2
(45) Date of Patent: Dec. 27, 2016

(54) ORGANOMETALLIC COMPLEX AND ORGANIC LIGHT-EMITTING DIODE INCLUDING THE SAME

(71) Applicants: Soung-Wook Kim, Yongin (KR);
Jae-Hong Kim, Yongin (KR);
Myeong-Suk Kim, Yongin (KR);
Moon-Jae Lee, Yongin (KR); Sung-Ho Jin, Yongin (KR)

(72) Inventors: Soung-Wook Kim, Yongin (KR);
Jae-Hong Kim, Yongin (KR);
Myeong-Suk Kim, Yongin (KR);
Moon-Jae Lee, Yongin (KR); Sung-Ho Jin, Yongin (KR)

(73) Assignees: SAMSUNG DISPLAY CO., LTD., Yongin, Gyeonggi-do (KR); PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 575 days.

(21) Appl. No.: 14/018,558

(22) Filed: Sep. 5, 2013

(65) Prior Publication Data
US 2014/0209873 A1 Jul. 31, 2014

(30) Foreign Application Priority Data
Jan. 30, 2013 (KR) ........................ 10-2013-0010718

(51) Int. Cl.
| | | |
|---|---|---|
| H01L 51/54 | (2006.01) | |
| C09K 11/06 | (2006.01) | |
| H01L 51/00 | (2006.01) | |
| C07F 15/00 | (2006.01) | |
| H01L 51/50 | (2006.01) | |

(52) U.S. Cl.
CPC ....... *H01L 51/0085* (2013.01); *C07F 15/0033* (2013.01); *C09K 11/06* (2013.01); *C09K 2211/1029* (2013.01); *C09K 2211/1044* (2013.01); *C09K 2211/185* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 7,329,898 B2 | 2/2008 | Igarashi | |
| 2002/0024293 A1* | 2/2002 | Igarashi et al. ..... | C07F 15/0033 313/483 |
| 2004/0253478 A1* | 12/2004 | Thompson et al. . | C07D 231/12 428/690 |
| 2007/0292713 A9 | 12/2007 | Dobbs et al. | |
| 2012/0235132 A1* | 9/2012 | Terashima et al. . | C07F 15/0033 257/40 |

FOREIGN PATENT DOCUMENTS

| | | |
|---|---|---|
| KR | 10-2010-0110958 A | 10/2010 |
| KR | 10-1066743 B1 | 9/2011 |
| WO | WO 2010/093176 A2 | 8/2010 |
| WO | WO 2011/065454 A1 * | 6/2011 |

OTHER PUBLICATIONS

Forsythe, E. W., et al., "Organic Light Emitting Devices and Materials Integrated With Active Matrix Backplanes for Flexible Displays," Sensors and Electron Devices Directorate, Army Research Laboratory, Adelphi, MD, Nov. 1, 2006, pp. 1-3.

* cited by examiner

*Primary Examiner* — Marie R. Yamnitzky
(74) *Attorney, Agent, or Firm* — Lee & Morse, P.C.

(57) ABSTRACT

Embodiments are directed to an organometallic complex and an organic light-emitting diode including the organometallic complex. The organometallic complex may be represented by Formula 1:

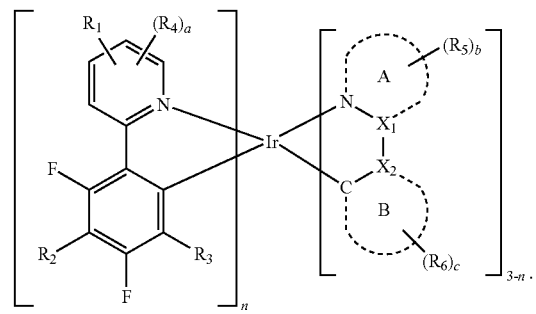

7 Claims, 9 Drawing Sheets

ORGANOMETALLIC COMPLEX AND ORGANIC LIGHT-EMITTING DIODE INCLUDING THE SAME

CROSS-REFERENCE TO RELATED APPLICATION

This application claims the benefit of and priority under 35 U.S.C. §119 to Korean Patent Application No. 10-2013-0010718 filed on Jan. 30, 2013, in the Korean Intellectual Property Office, and entitled: "ORGANOMETALLIC COMPLEX AND ORGANIC LIGHT-EMITTING DIODE INCLUDING THE SAME," which is incorporated by reference herein in its entirety.

BACKGROUND

1. Field

Embodiments relate to an organometallic complex and an organic light-emitting diode including the same.

2. Description of the Related Art

Organic light-emitting diodes (OLEDs), which are self-emitting diodes, have advantages such as wide viewing angles, excellent contrast, quick response, high brightness, and excellent driving voltage characteristics, and can provide multicolored images.

SUMMARY

Embodiments are directed to an organometallic complex represented by Formula 1 below:

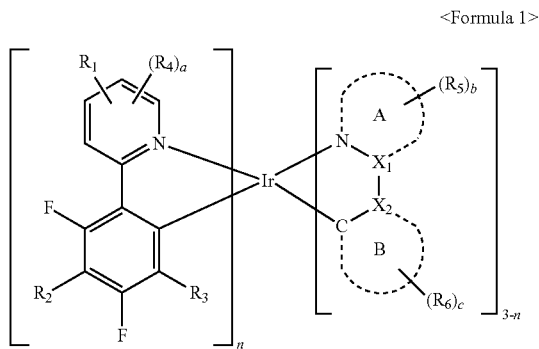

<Formula 1> in Formula 1, $R_1$ is selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$), and —Si($Q_4$)($Q_5$)($Q_6$), in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group;

$R_2$ to $R_6$ are each independently selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$), and —Si($Q_4$)($Q_5$)($Q_6$), in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group;

a is an integer of 1 to 3, and when a is 2 or more, 2 or more of $R_4$ may be identical to or different from each other; and b and c are each independently an integer of 1 to 6, and when b is 2 or more, 2 or more of $R_5$ may be identical to or different from each other, and when c is 2 or more, 2 or more of $R_6$ may be identical to or different from each other;

Ring A is selected from pyrrol, imidazole, pyrazole, triazole, thiazole, oxazole, isothiazole, isoxazole, benzothiazole, benzoimidazole, benzooxazole, pyridine, pyrazine, pyrimidine, pyridazine, isoindole, indole, indazole, purine, isoquinoline, quinoline, phthalazine, naphthyridine, quinoxaline, quinazoline, cinnoline, phenanthridine, acridine, phenanthroline, and phenoxazine;

Ring B is selected from benzene, pentalene, indene, naphtalene, azulene, heptalene, indacene, acenaphthylene, fluorene, spiro-fluorene, phenalene, phenanthrene, anthracene, fluoranthene, triphenylene, pyrene, chrysene pyrrol, imidazole, pyrazole, triazole, isothiazole, isoxazole, pyridine, pyrazine, pyrimidine, pyridazine, isoindole, indole, indazole, purine, isoquinoline, quinoline, phthalazine, naphthyridine, quinoxaline, quinazoline, cinnoline, phenanthridine, acridine, phenanthroline, and phenoxazine;

$X_1$ and $X_2$ are each independently N or C; and n is 1 or 2.

Embodiments are also directed to an organic light-emitting diode including a substrate, a first electrode, a second electrode facing the first electrode, and an organic layer that is interposed between the first electrode and the second electrode and includes an emission layer, wherein the organic layer includes one or more of the organometallic complex.

BRIEF DESCRIPTION OF THE DRAWINGS

Features will become apparent to those of skill in the art by describing in detail example embodiments with reference to the attached drawings in which.

DETAILED DESCRIPTION

Figure 1:
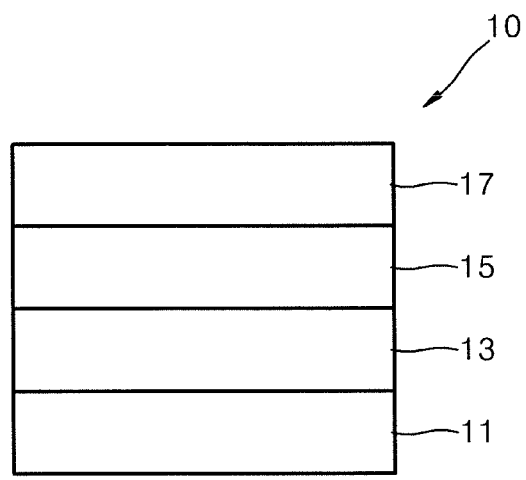
FIG. 1 is a cross-sectional view of the structure of an organic light-emitting diode according to an example embodiment.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey the scope of the example embodiments to those skilled in the art.

As used herein, the term "and/or" includes any and all combinations of one or more of the associated listed items. Expressions such as "at least one of," and "at least one selected from," when preceding a list of elements, modify the entire list of elements and do not modify the individual elements of the list.

An organometallic complex according to an example embodiment is represented by Formula 1 below:

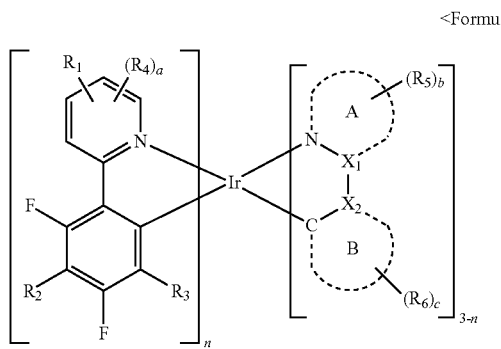

<Formula 1> in Formula 1, $R_1$ may be selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$), and —Si($Q_4$)($Q_5$)($Q_6$), in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group; $R_2$ to $R_6$ each independently may be selected from a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, a substituted or unsubstituted $C_2$-$C_{30}$ heteroaryl group, —N($Q_1$)($Q_2$), —C(=O)($Q_3$) and —Si($Q_4$)($Q_5$)($Q_6$), in which $Q_1$ to $Q_6$ are each independently a hydrogen atom, a substituted or unsubstituted $C_1$-$C_{60}$ alkyl group, a substituted or unsubstituted $C_6$-$C_{30}$ aryl group, or a substituted or unsubstituted $C_2$-$C_{30}$ heteroaryl group.

For example, in Formula 1, $R_1$ may be selected from:

a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{14}$ aryl group and a $C_2$-$C_{14}$ heteroaryl group; and a $C_6$-$C_{14}$ aryl group and a $C_2$-$C_{14}$ heteroaryl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group, and a $C_2$-$C_{14}$ heteroaryl group;

—N($Q_1$)($Q_2$); and

—C(=O)($Q_3$);

$R_2$ to $R_6$ each independently may be selected from:

a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{14}$ aryl group and a $C_2$-$C_{14}$ heteroaryl group;

a $C_6$-$C_{14}$ aryl group and a $C_2$-$C_{14}$ heteroaryl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group and a $C_2$-$C_{14}$ heteroaryl group;

—N($Q_1$)($Q_2$); and

—C(=O)($Q_3$).

In this regard, $Q_1$ to $Q_3$ each independently may be selected from a hydrogen atom, a $C_1$-$C_{20}$ alkyl group, a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{14}$ aryl group and a $C_2$-$C_{14}$ heteroaryl group; and a $C_6$-$C_{14}$ aryl group and a $C_2$-$C_{14}$ heteroaryl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group substituted with at least one F, a $C_1$-$C_{20}$ alkyl group, a $C_1$-$C_{20}$ alkoxy group, a $C_6$-$C_{14}$ aryl group, and a $C_2$-$C_{14}$ heteroaryl group.

According to an example embodiment, in Formula 1, $R_1$ may be selected from:

a deuterium atom, F, Cl, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a methyl group, an ethyl group, a propyl group, a n-butyl group, an isobutyl group, a sec-butyl group, a tert-butyl group, a n-pentyl group, a isopentyl group, a sec-pentyl group, a tert-pentyl group, a n-hexyl group, a isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group;

a methyl group, an ethyl group, a propyl group, a n-butyl group, an isobutyl group, a sec-butyl group, a tert-butyl group, a n-pentyl group, a isopentyl group, a sec-pentyl group, a tert-pentyl group, a n-hexyl group, a isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one selected from a deuterium atom, F, Cl, a hydroxyl group, a cyano group, a nitro group, an amino group, an amidino group, hydrazine, hydrazone, a carboxyl group or a salt thereof, a sulfonic acid or a salt thereof, and a phosphoric acid or a salt;

a phenyl group, a naphthyl group, an anthryl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group;

a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group, each substituted with at least one selected from a deuterium atom, F, Cl, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group;

—N($Q_1$)($Q_2$); and

—C(=O)($Q_3$), $R_2$ to $R_6$ each independently may be selected from:

a hydrogen atom, a deuterium atom, F, Cl, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group;

a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one selected from a deuterium atom, F, Cl, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group;

a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group, each substituted with at least one selected from a deuterium atom, F, Cl, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group;

—N($Q_1$)($Q_2$); and

—C(=O)($Q_3$).

In this regard, $Q_1$ to $Q_3$ each independently may be selected from:

a methyl group, an ethyl group, a propyl group, a n-butyl group, an isobutyl group, a sec-butyl group, a tert-butyl group, a n-pentyl group, an isopentyl group, a sec-a pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group;

a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one selected from a deuterium atom, F, Cl, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group; and a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group and a carbazolyl group, each substituted with at least one selected from a deuterium atom, F, Cl, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group substituted with at least one F (for example, —$CF_3$ or the like), a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl.

For example, in Formula 1, $R_1$ may be selected from a methyl group, an ethyl group, a propyl group, a n-butyl group, an isobutyl group, a sec-butyl group, a tert-butyl group, a n-pentyl group, a isopentyl group, a sec-pentyl group, a tert-pentyl group, a n-hexyl group, a isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, and —$N(Q_1)(Q_2)$, in which $Q_1$ and $Q_2$ each independently may be selected from a methyl group, an ethyl group, a propyl group, a n-butyl group, an isobutyl group, a sec-butyl group, a tert-butyl group, a n-pentyl group, a isopentyl group, a sec-pentyl group, a tert-pentyl group, a n-hexyl group, a isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and tert-decanyl;

a phenyl group, a naphthyl group, an anthryl group, a pyrenyl group, a phenanthrenyl group and a fluorenyl group; and a phenyl group, a naphthyl group, an anthryl group, a pyrenyl group, a phenanthrenyl group, and a fluorenyl group, each substituted with at least one selected from a deuterium atom, F, Cl, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group.

Also, in Formula 1, $R_2$ may be selected from a hydrogen atom, a halogen atom, a cyano group, a nitro group; a $C_1$-$C_{60}$ alkyl group substituted with at least one halogen atom; a $C_6$-$C_{30}$ aryl group and a $C_2$-$C_{30}$ heteroaryl group, each substituted with at least one halogen atom; and —$C(=O)(Q_3)$, in which $Q_3$ may be selected from a $C_1$-$C_{60}$ alkyl group substituted with at least one halogen atom; and a $C_6$-$C_{30}$ aryl group and a $C_2$-$C_{30}$ heteroaryl group, each substituted with at least one selected from a halogen atom and a $C_1$-$C_{20}$ alkyl group substituted with at least one halogen atom.

For example, in Formula 1, $R_2$ may be selected from:

a hydrogen atom, F, Cl, a cyano group, a nitro group;

a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one F; and a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group and a carbazolyl group, each substituted with at least one F; and —$C(=O)(Q_3)$ in which $Q_1$ to $Q_3$ each independently may be a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one F; and a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group, each substituted with at least one selected from F and a $C_1$-$C_{20}$ alkyl group substituted with at least one F.

$R_3$ in Formula 1 may be a hydrogen atom.

a in Formula 1 indicates the number of $R_4$, and a may be an integer of 1 to 3, and when a is 2 or more, 2 or more of $R_4$ may be identical to or different from each other.

b and c in Formula 1 are each independently an integer of 1 to 6, when b is 2 or more, 2 or more of $R_5$ may be identical to or different from each other, and when c is 2 or more, 2 or more of $R_6$ may be identical to or different from each other. b indicates the number of $R_5$, and $R_5$ is a substituent of ring A in Formula 1. When $R_5$ is a hydrogen atom, ring A in Formula 1 may be an unsubstituted ring. c indicates the number of $R_6$, and $R_6$ is a substituent of ring B in Formula 1. When $R_6$ is a hydrogen atom, ring B in Formula 1 may be an unsubstituted ring.

Ring A in Formula 1 may be selected from pyrrol, imidazole, pyrazole, triazole, thiazole, oxazole, isothiazole, isoxazole, benzothiazole, benzoimidazole, benzooxazole, pyridine, pyrazine, pyrimidine, pyridazine, isoindole, indole, indazole, purine, isoquinoline, quinoline, phthalazine, naphthyridine, quinoxaline, quinazoline, cinnoline, phenanthridine, acridine, phenanthroline, phenazine, and phenoxazine.

Also, ring B in Formula 1 may be selected from benzene, pentalene, indene, naphtalene, azulene, heptalene, indacene, acenaphthylene, fluorene, spiro-fluorene, phenalene, phenanthrene, anthracene, fluoranthene, triphenylene, pyrene, chrysene pyrrol, imidazole, pyrazole, triazole, isothiazole, isoxazole, pyridine, pyrazine, pyrimidine, pyridazine, isoindole, indole, indazole, purine, isoquinoline, quinoline, phthalazine, naphthyridine, quinoxaline, quinazoline, cinnoline, phenanthridine, acridine, phenanthroline and phenoxazine.

For example, ring A in Formula 1 may be pyridine, pyrimidine, pyrazine, or pyrazole, but is not limited thereto. According to an example embodiment, ring A in Formula 1 may be pyridine or pyrazole.

Ring B in Formula 1 may be benzene or naphthalene, but is not limited thereto. According to an example embodiment, ring B may be benzene, but is not limited thereto.

$X_1$ and $X_2$ in Formula 1 may be each independently N or C. According to an example embodiment, $X_1$ is independently N or C and $X_2$ is C.

The organometallic complex may be represented by Formula 1A below:

<Formula 1A>

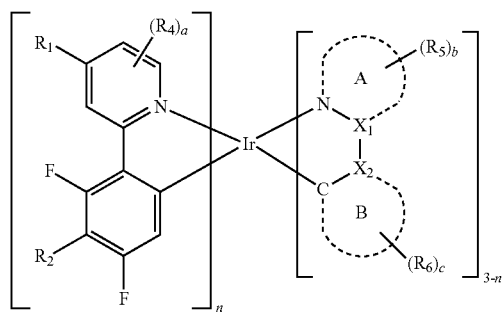

$R_1$, $R_2$, and $R_4$ to $R_6$, a, b, c, ring A, ring B, $X_1$, $X_2$ and n in Formula 1A may be as defined above.

According to another embodiment, the organometallic complex may be represented by Formula 2A or 2B below, but is not limited thereto:

<Formula 2A>

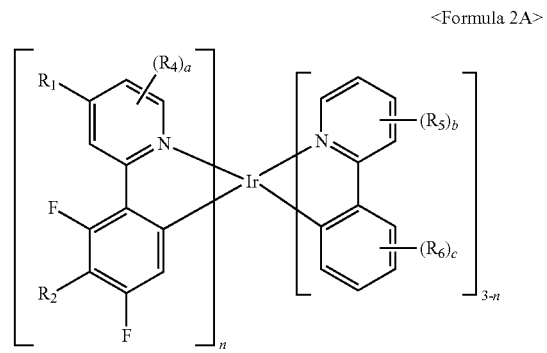

<Formula 2B>

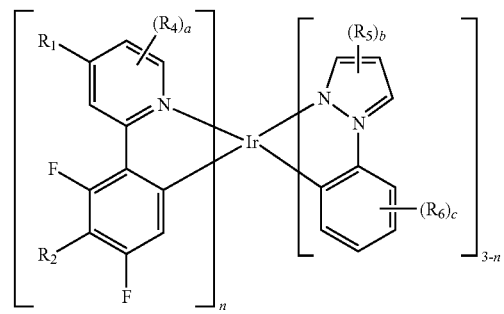

$R_1$, $R_2$, $R_4$ to $R_6$, a, b, c and n in Formulae 2A and 2B may be as defined above.

For example, in Formulae 2A and 2B, $R_1$ may be selected from:

a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a $C_6$-$C_{14}$ aryl group and a $C_2$-$C_{14}$ heteroaryl group;

a $C_6$-$C_{14}$ aryl group and a $C_2$-$C_{14}$ heteroaryl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group and a $C_2$-$C_{14}$ heteroaryl group;

—N($Q_1$)($Q_2$); and

—C(=O)($Q_3$); and $R_2$ and $R_4$ to $R_6$ each independently may be selected from:

a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof;

a $C_6$-$C_{14}$ aryl group and a $C_2$-$C_{14}$ heteroaryl group;

a $C_6$-$C_{14}$ aryl group and a $C_2$-$C_{14}$ heteroaryl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, a $C_1$-$C_{20}$ alkoxy group, a $C_6$-$C_{14}$ aryl group, and a $C_2$-$C_{14}$ heteroaryl group;

—$N(Q_1)(Q_2)$; and

—$C(=O)(Q_3)$, in which $Q_1$ to $Q_3$ each independently may be selected from:

a hydrogen atom, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof;

a $C_6$-$C_{14}$ aryl group and a $C_2$-$C_{14}$ heteroaryl group; and a $C_6$-$C_{14}$ aryl group and a $C_2$-$C_{14}$ heteroaryl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group substituted with at least one F, a $C_1$-$C_{20}$ alkyl group, a $C_1$-$C_{20}$ alkoxy group, a $C_6$-$C_{14}$ aryl group, and a $C_2$-$C_{14}$ heteroaryl group, and a, b and c are each independently an integer of 1 to 3, when a is 2 or more, 2 or more of $R_4$ may be identical to or different from each other, when b is 2 or more, 2 or more of $R_5$ may be identical to or different from each other, and when c is 2 or more, 2 or more of $R_6$ may be identical to or different from each other, and n may be 1 or 2.

According to another embodiment, in Formulae 2A and 2B, $R_1$ may be a methyl group, an ethyl group, a propyl group, a n-butyl group, an isobutyl group, a sec-butyl group, a tert-butyl group, a n-pentyl group, a isopentyl group, a sec-pentyl group, a tert-pentyl group, a n-hexyl group, a isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, a tert-decanyl group, and —$N(Q_1)(Q_2)$, $R_2$ may be selected from a hydrogen atom, F, Cl, a cyano group, a nitro group; a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one F; a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group, each substituted with at least one F; and —$C(=O)(Q_3)$, in which $Q_1$ to $Q_3$ each independently may be selected from a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonenyl group, an isononenyl group, a sec-nonenyl group, a tert-nonenyl group, a n-decanyl group, an isodecanyl group, a sec-decanyl group, and a tert-decanyl group, each substituted with at least one F; and a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group and a carbazolyl group, each substituted with at least one selected from F and a $C_1$-$C_{20}$ alkyl group substituted with at least one F, and $R_4$ to $R_6$ may be a hydrogen atom, but are not limited thereto.

The organometallic complex may include at least one selected from complexes 1 to 16 below, but is not limited thereto:

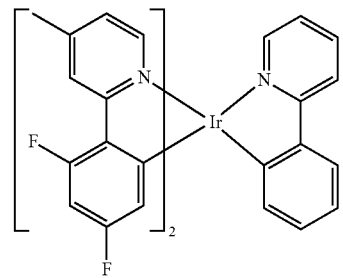

1

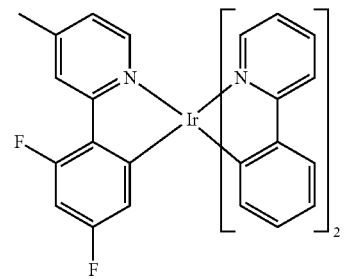

2

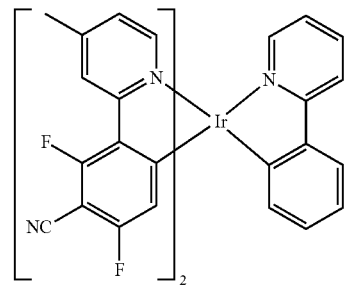

3

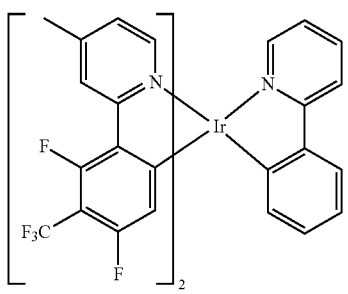
4
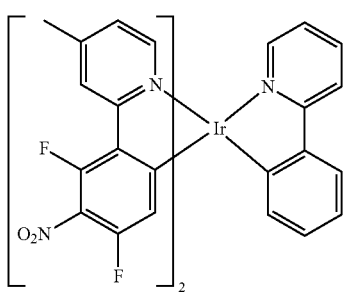
5
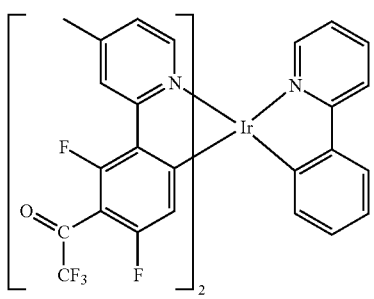
6
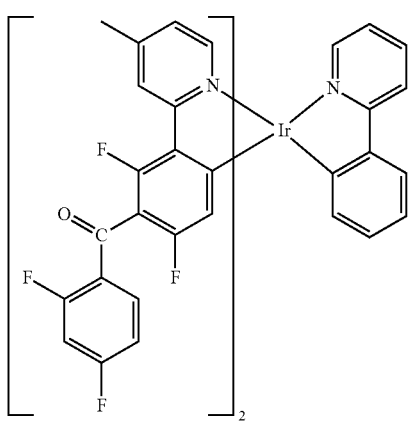
7
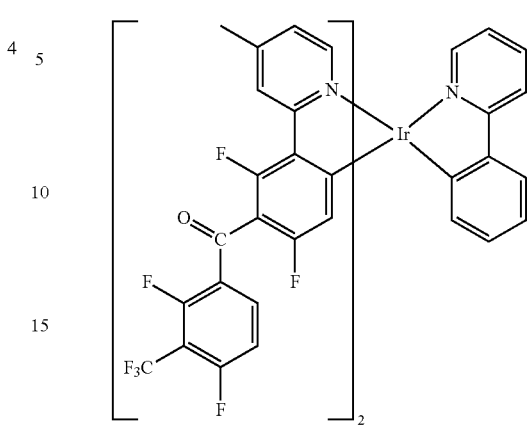
8
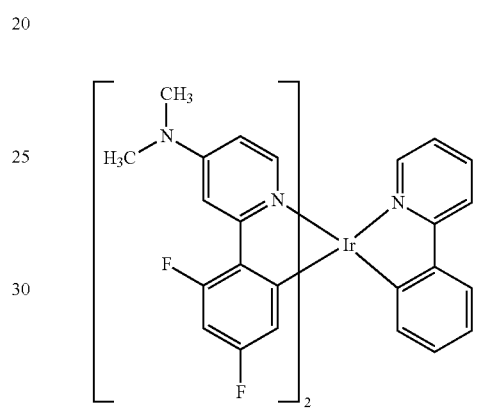
9
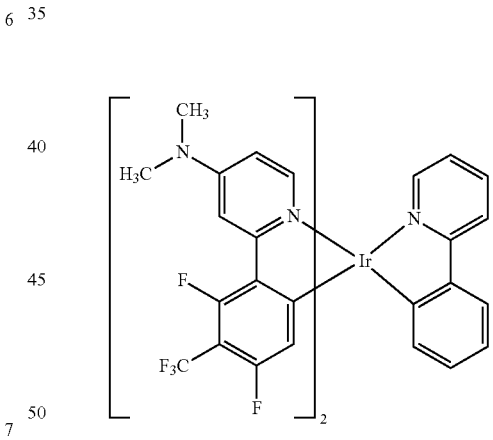
10
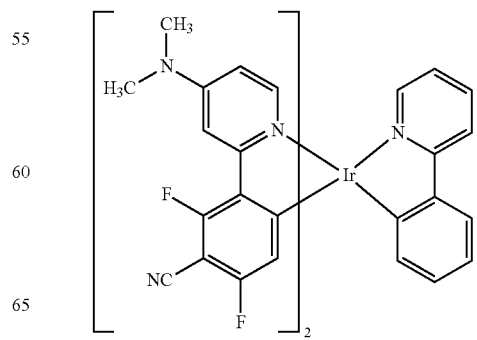
11

-continued

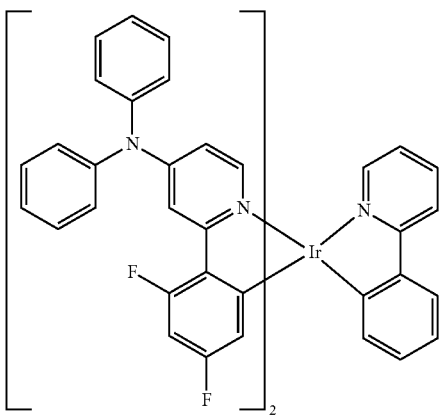

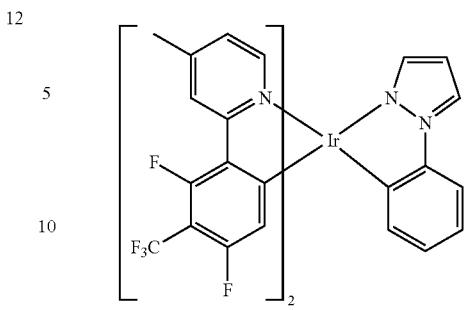

The organometallic complex may include a first fluorine and a second fluorine as illustrated in Formula 1', and accordingly, an electron density of a benzene ring combined with the first fluorine and the second fluorine (which are electron withdrawing groups), decreases. As a result, light emitted by the organometallic complex may be light that is shifted toward a shorter wavelength region, that is, a blue region. Also, a ligand of the organometallic complex may easily trap electrons, and many excited excitons may be formed together with holes injected into an emission layer. Thus, an organic light-emitting diode including the organometallic complex may have high luminescent efficiency.

Also, a pyridine ring in the ligand in the Formula 1 may includes a $R_1$ substituent, such as, e.g., an alkyl group, and thus an electron density of the pyridine ring may be controlled, and accordingly, the emission color may easily shift toward a shorter wavelength region or a longer wavelength region, and quantities of electrons or holes to be trapped may be controlled. Accordingly, an organic light-emitting diode including the organometallic complex may have high luminescent efficiency.

In addition, when $R_2$ in Formula 1' is an electron withdrawing group, an electron density of a benzene ring combined with $R_2$ may be further lowered. As a result, light emitted by the organometallic complex may be a green light that is shifted toward a shorter wavelength region, that is, a blue region. Also, a ligand of the organometallic complex may easily trap electrons, and many excited excitons may be formed together with holes injected into an emission layer. Thus, an organic light-emitting diode including the organometallic complex may have high luminescent efficiency.

Accordingly, the organometallic complex represented by Formula 1 may emit various tuned color of light, and may also provide luminescent efficiency.

The organometallic complex of Formula 1 may be synthesized by using a suitable organic synthesis method. Examples of the organometallic complex synthesis method are described later.

At least one of the organometallic complexes of Formula 1 may be used between a pair of electrodes of an organic light-emitting diode. For example, at least one of the organometallic complexes may be used in an emission layer.

Accordingly, an organic light-emitting diode including a first electrode, a second electrode facing the first electrode, and an organic layer that is interposed between the first electrode and the second electrode and includes an emission layer, in which the organic layer includes at least one of the organometallic complexes of Formula 1.

The phrase: "an (organic layer) includes at least one of the organometallic complex" used herein means that an "(organic layer) may include one kind of the organometallic complex of Formula 1, or two or more different kinds of the organometallic complex of Formula 1."

For example, the organic layer may include only Complex 1 as the organometallic complex. In this regard, Complex 1 may be present in the emission layer of the organic light-emitting diode. According to another embodiment, the organic layer may include Complex 1 and Complex 2 as the organometallic complex. In this regard, Complex 1 and Complex 2 may be present in an identical layer (for example, the emission layer).

The organic layer may further include, i) between the first electrode and the emission layer, at least one layer selected from a hole injection layer, a hole transport layer, a functional layer (hereinafter referred to as a "H-functional layer") having a hole injection function and a hole transportation function, a buffer layer, and an electron blocking layer, and ii) between the emission layer and the second electrode, at least one layer selected from a hole blocking layer, an electron transport layer, and an electron injection layer.

The term "organic layer" used herein refers to a single layer and/or a multi layer interposed between the first electrode and the second electrode of the organic light-emitting diode.

The organic layer may include an emission layer, and the emission layer may include at least one organometallic complex described above.

The organometallic complex included in the emission layer may act as a phosphorescent dopant, and the emission layer may further include a host. Examples of the host are presented below.

The organic light-emitting diode including the organometallic complex described above may emit green light, for example, green phosphorescent light.

FIG. 1 is a schematic sectional view of an organic light-emitting device 10 according to an example embodiment. Hereinafter, the structure and manufacturing method of an organic light-emitting device according to an example embodiment is described in detail with reference to FIG. 1.

A substrate 11, which may be any substrate that is used in general organic light-emitting devices, may be a glass substrate or a transparent plastic substrate with excellent mechanical strength, thermal stability, transparency, surface smoothness, ease of handling, and water resistance.

A first electrode 13 may be formed by, for example, depositing or sputtering a material for a first electrode on the substrate 11. When the first electrode 13 is an anode, the material for the first electrode may be selected from materials with a high work function to enable ease of hole injection. The first electrode 13 may be a reflective electrode or a transmission electrode. The material for the first electrode may be a transparent material with high conductivity, and examples of such a material are indium tin oxide (ITO), indium zinc oxide (IZO), tin oxide ($SnO_2$), and zinc oxide (ZnO). When magnesium (Mg), aluminum (Al), aluminum-lithium (Al—Li), calcium (Ca), magnesium-indium (Mg—In), magnesium-silver (Mg—Ag), or the like is used, the first electrode 13 may be used as a reflective electrode.

The first electrode 13 may have a single-layer structure or a multi-layer structure including at least two layers. For example, the first electrode 13 may have a three-layered structure of ITO/Ag/ITO, but is not limited thereto.

The organic layer 15 may be disposed on the first electrode 13.

An organic layer 15 may include a hole injection layer, a hole transport layer, a buffer layer, an emission layer, an electron transport layer, and an electron injection layer.

A hole injection layer (HIL) may be formed on the first electrode 13 by using various methods, such as vacuum deposition, spin coating, casting, Langmuir-Blodgett (LB) deposition.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ ton to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

As a hole injection material, a suitable hole injection material may be used, and examples thereof are N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine(NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (pani/CSA), or (polyaniline)/poly(4-styrenesulfonate) (PANI/PSS) may be used, but the hole injection material is not limited thereto: Alternatively, as a suitable hole injection material, for example, N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine(NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (pani/CSA), or (polyaniline)/poly(4-styrenesulfonate) (PANI/PSS) may be used, but the hole injection material is not limited thereto:

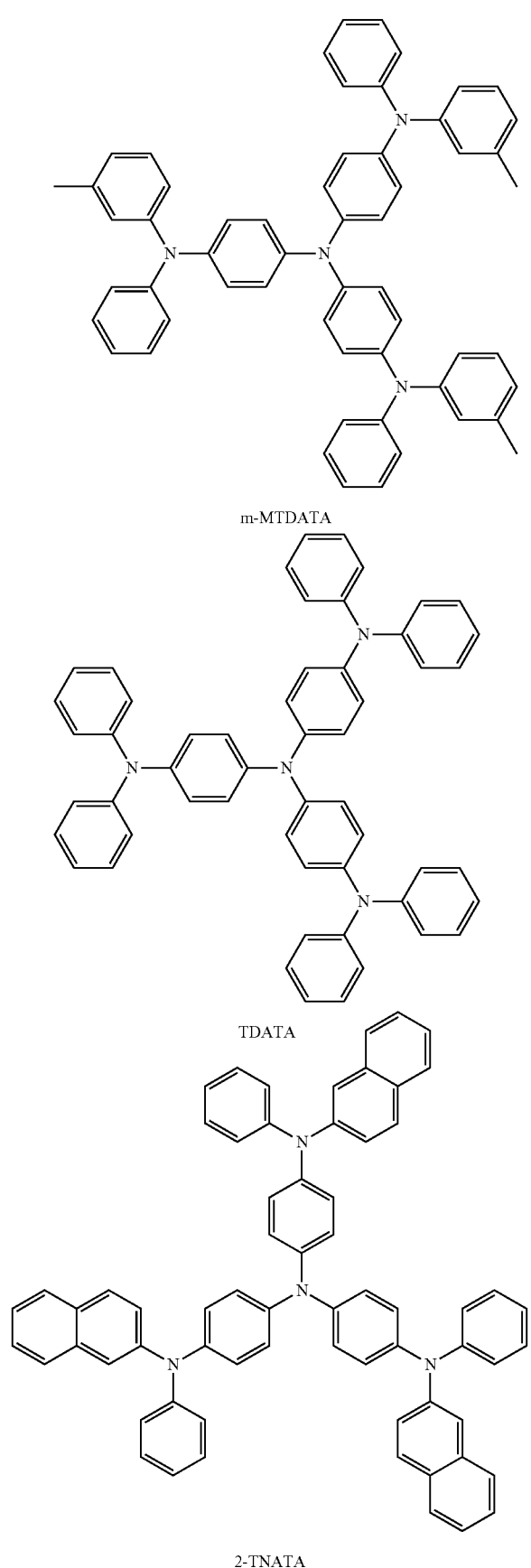

m-MTDATA

TDATA

2-TNATA

A thickness of the HIL may be in a range of about 100 Å to about 10000 Å, for example, about 100 Å to about 1000 Å. When the thickness of the HIL is within the range described above, the HIL may have satisfactory hole injection characteristics without a substantial increase in a driving voltage.

Then, a hole transport layer (HTL) may be formed on the HIL by using vacuum deposition, spin coating, casting, LB deposition, or the like. When the HTL is formed using vacuum deposition or spin coating, the deposition and coating conditions may be similar to those for the formation of the HIL, though the deposition and coating conditions may vary according to a compound that is used to form the HTL.

As a hole transport material, a suitable hole transport material may be used, and examples thereof are a carbazole derivative, such as N-phenylcarbazole, or polyvinylcarbazole, N,N'-bis(3-methylphenyl)-N,N'-diphenyl-[1,1-biphenyl]-4,4'-diamine (TPD), 4,4',4"-tris(N-carbazolyl)triphenylamine (TCTA), N,N'-di(1-naphthyl)-N,N'-diphenylbenzidine (NPB), or the like may be used, but the hole transport material is not limited thereto.

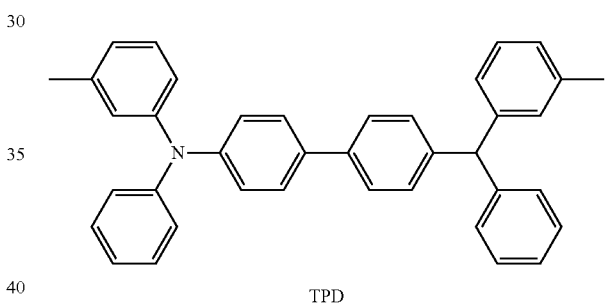

TPD

A thickness of the HTL may be in a range of about 50 Å to about 2000 Å, for example, about 100 Å to about 1500 Å. When the thickness of the HTL is within the range described above, the HTL may have satisfactory hole transport characteristics without a substantial increase in a driving voltage.

The H-functional layer (a functional layer having a hole injection ability and a hole transport ability) may include one or more materials selected from the materials for the HIL and the materials for the HTL. A thickness of the H-functional layer may be in a range of about 100 Å to about 10000 Å, for example, about 100 Å to about 1000 Å. When the thickness of the H-functional layer is within the range described above, the H-functional layer may have satisfactory hole injection and transport characteristics without a substantial increase in a driving voltage.

In addition, at least one layer of the hole injection layer, the hole transport layer, and the H-functional layer may include at least one selected from a compound represented by Formula 300 below and a compound represented by Formula 350 below:

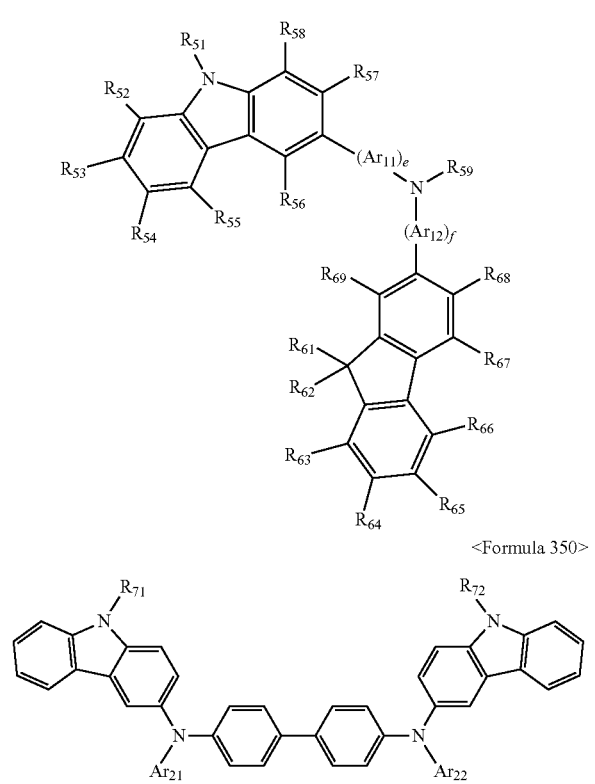

<Formula 300>

<Formula 350>

Ar$_{11}$ and Ar$_{12}$ in Formula 300 may be each independently a substituted or unsubstituted C$_6$-C$_{60}$ arylene group. For example, Ar$_{11}$ and Ar$_{12}$ are each independently a substituted or unsubstituted phenylene group, a substituted or unsubstituted naphthylene group, a substituted or unsubstituted fluorenylene group, or a substituted or unsubstituted anthrylene group, but are not limited thereto. At least one substituent of at least one of the substituted phenylene group, the substituted naphthylene group, the substituted fluorenylene group, and the substituted anthrylene group may be a deuterium atom, a halogen atom, a hydroxyl group, a cyano group, a C$_1$-C$_{20}$ alkyl group, a C$_1$-C$_{20}$ alkoxy group, a phenyl group, a naphthyl group, an anthryl group, a carbazolyl group, or a phenyl-substituted carbazolyl group, but is not limited thereto.

Ar$_{21}$ and Ar$_{22}$ in Formula 350 may be each independently a substituted or unsubstituted C$_6$-C$_{60}$ aryl group, or a substituted or unsubstituted C$_2$-C$_{60}$ heteroaryl group. For example, Ar$_{21}$ and Ar$_{22}$ may be each independently selected from a substituted or unsubstituted phenyl group, a substituted or unsubstituted naphthyl group, a substituted or unsubstituted phenanthrenyl group, a substituted or unsubstituted anthryl group, a substituted or unsubstituted a pyrenyl group, a substituted or unsubstituted chrycenyl group, a substituted or unsubstituted a fluorenyl group, a substituted or unsubstituted a carbazolyl group, a substituted or unsubstituted dibenzofuranyl group, or a substituted or unsubstituted dibenzothiophenyl group. In this regard, at least one substituent of the substituted phenyl group, the substituted naphthyl group, the substituted phenanthrenyl group, the substituted anthryl group, the substituted pyrenyl group, the substituted chrycenyl group, the substituted fluorenyl group, the substituted carbazolyl group, the substituted dibenzofuranyl group, and the substituted dibenzothiophenyl group may be selected from:

a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a C$_1$-C$_{10}$ alkyl group, a C$_1$-C$_{10}$ alkoxy group, a phenyl group, a naphthyl group, a fluorenyl group, a phenanthrenyl group, an anthryl group, a triphenylenyl group, a pyrenyl group, a chrycenyl group, an imidazolyl group, an imidazolinyl group, an imidazopyridinyl group, an imidazopyrimidinyl group, a pyridinyl group, a pyrazinyl group, a pyrimidinyl group, and an indolyl group; and a phenyl group, a naphthyl group, a fluorenyl group, a phenanthrenyl group, an anthryl group, a triphenylenyl group, a pyrenyl group, a chrycenyl group, an imidazolyl group, an imidazolinyl group, an imidazopyridinyl group, an imidazopyrimidinyl group, a pyridinyl group, a pyrazinyl group, a pyrimidinyl group, and an indolyl group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a C$_1$-C$_{10}$ alkyl group, and a C$_1$-C$_{10}$ alkoxy group.

e and f in Formula 300 may be each independently an integer of 0 to 5, or may be 0, 1, or 2. For example, e may be 1 and f may be 0, but e and f are not limited thereto.

R$_{51}$ to R$_{58}$, R$_{61}$ to R$_{69}$ and R$_{71}$ and R$_{72}$ in Formulae 300 and 350 are each independently a hydrogen atom, a deuterium atom, halogen atom, hydroxyl group, a cyano group, —NO$_2$, an amino group, an amidino group, hydrazine, hydrazone, a carboxyl group or a salt thereof, a sulfonic acid or a salt thereof, a phosphoric acid or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{60}$ cycloalkyl group, a substituted or unsubstituted C$_6$-C$_{60}$ aryl group, a substituted or unsubstituted C$_6$-C$_{60}$ aryloxy group, or a substituted or unsubstituted C$_6$-C$_{60}$ arylthio group. For example, R$_{51}$ to R$_{58}$, R$_{61}$ to R$_{69}$ and R$_{71}$ and R$_{72}$ may be each independently selected from:

a hydrogen atom, a deuterium atom, a halogen atom, a hydroxyl group, a cyano group, —NO$_2$, an amino group, an amidino group, hydrazine, hydrazone, a carboxyl group or a salt thereof, a sulfonic acid or a salt thereof, a phosphoric acid or a salt thereof; a C$_1$-C$_{10}$ alkyl group (for example, a methyl group, an ethyl group, a propyl group, a butyl group, a pentyl group, a hexyl group, or the like); a C$_1$-C$_{10}$ alkoxy group (for example, a methoxy group, an ethoxy group, a propoxy group, a butoxy group, a pentoxy group, or the like);

a C$_1$-C$_{10}$ alkyl group and a C$_1$-C$_{10}$ alkoxy group, each substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, and a phosphoric acid or a salt thereof;

a phenyl group; a naphthyl group; an anthryl group; a fluorenyl group; a pyrenyl group; and a phenyl group, a naphthyl group, an anthryl group, a fluorenyl group, and a pyrenyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{10}$ alkyl group, and a $C_1$-$C_{10}$ alkoxy group, but are not limited thereto.

$R_{59}$ in Formula 300 may be selected from:

a phenyl group; a naphthyl group; an anthryl group; a biphenyl group; a pyridyl group; and a phenyl group, a naphthyl group, an anthryl group, a biphenyl group and a pyridyl group, each substituted with at least one substituent selected from a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{20}$ alkyl group, and substituted or unsubstituted $C_1$-$C_{20}$ alkoxy group.

According to an example embodiment, the compound represented by Formula 300 may also be represented by Formula 300A below, but is not limited thereto:

<Formula 300A>

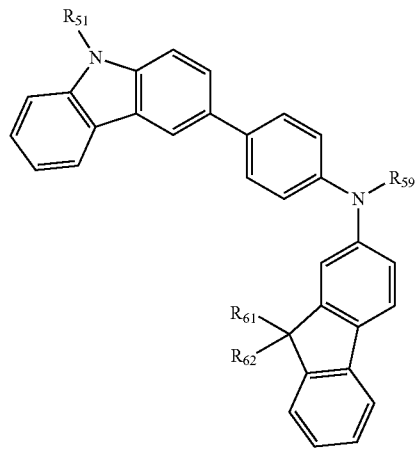

$R_{51}$, $R_{61}$, $R_{62}$, and $R_{59}$ in Formula 300A may be as described above.

For example, at least one layer selected from the hole injection layer, the hole transport layer, and the H-functional layer may include at least one selected from Compounds 301 to 320, but is not limited thereto:

301

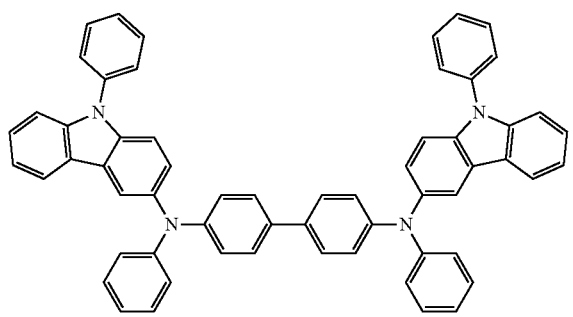

302

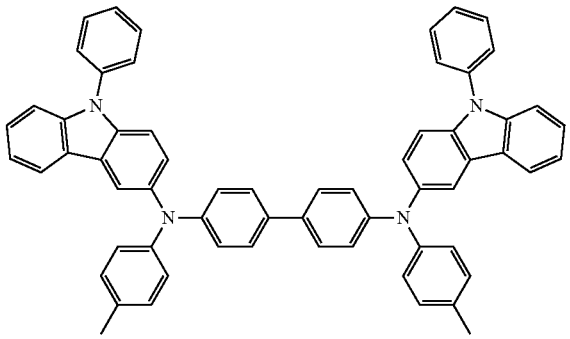

303

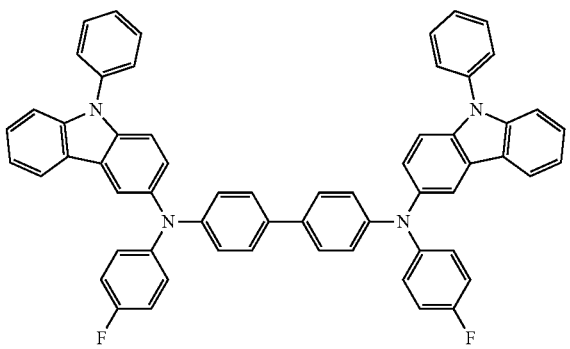

304

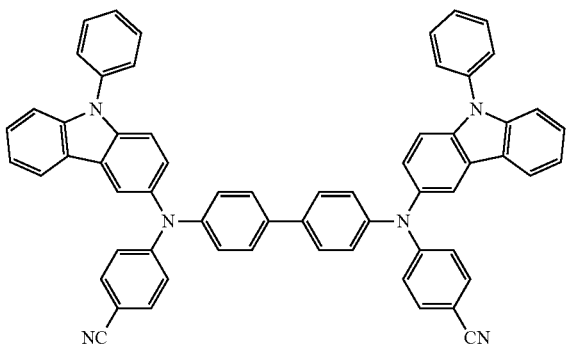

305

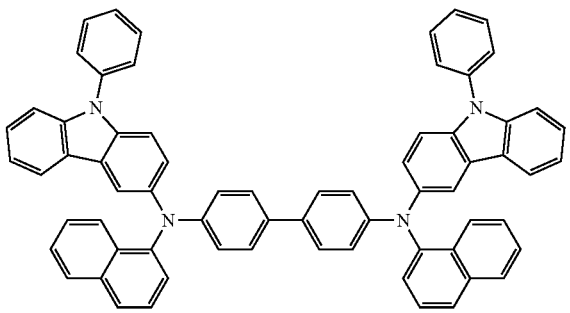

306
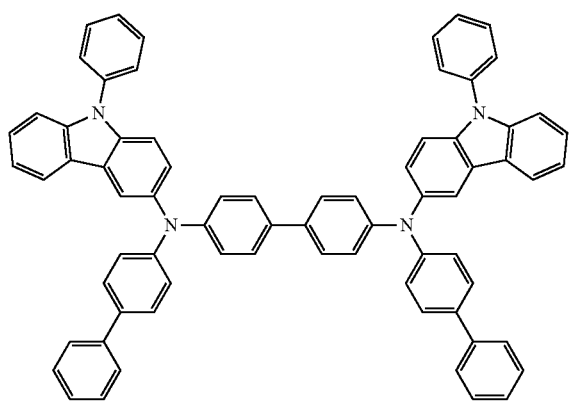
307
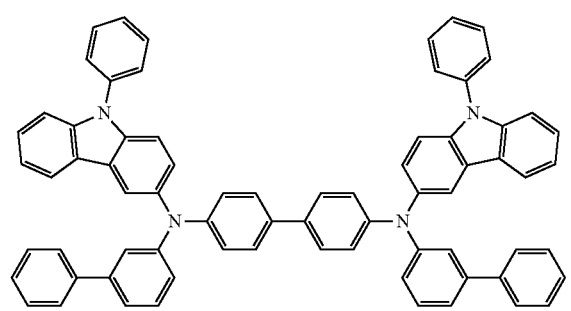
308
309
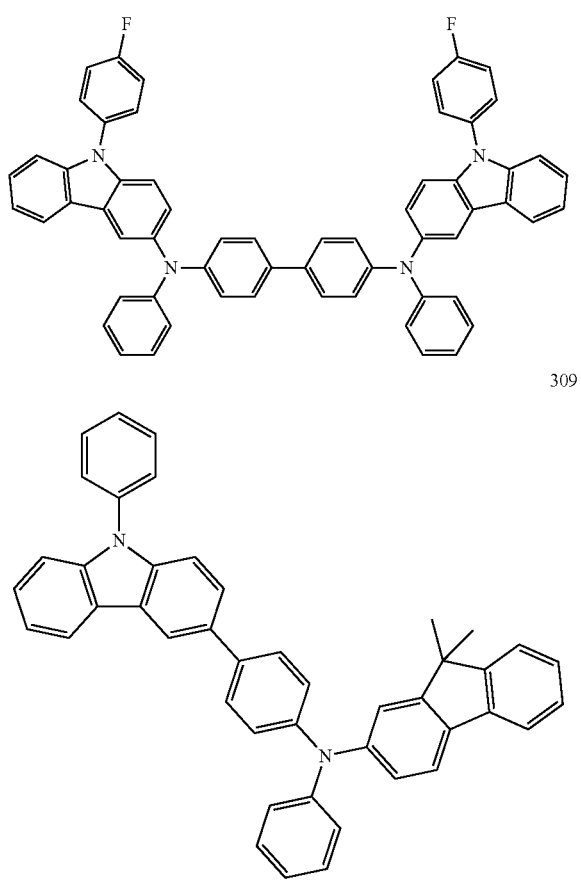
310
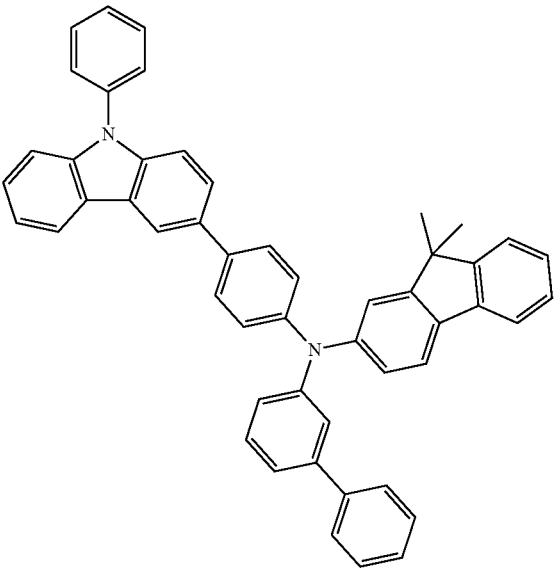
311
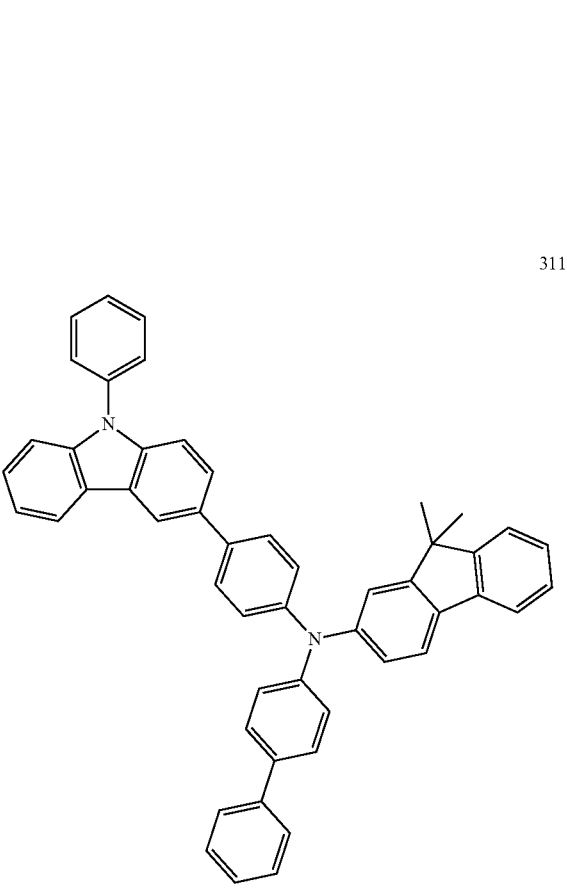

-continued
312
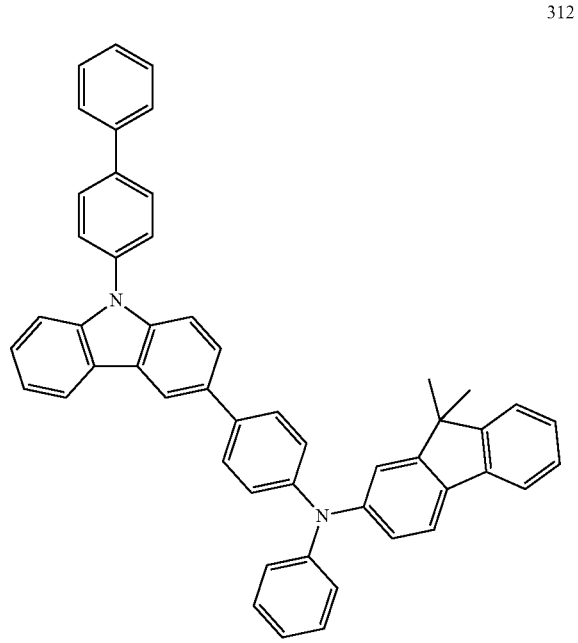
314
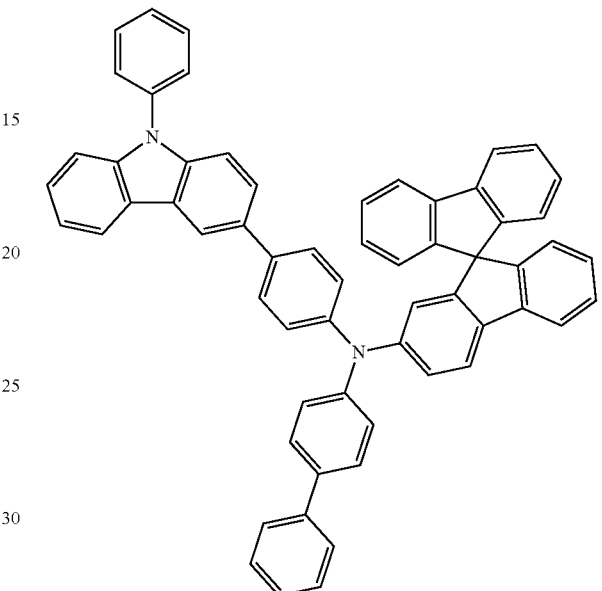
313
315
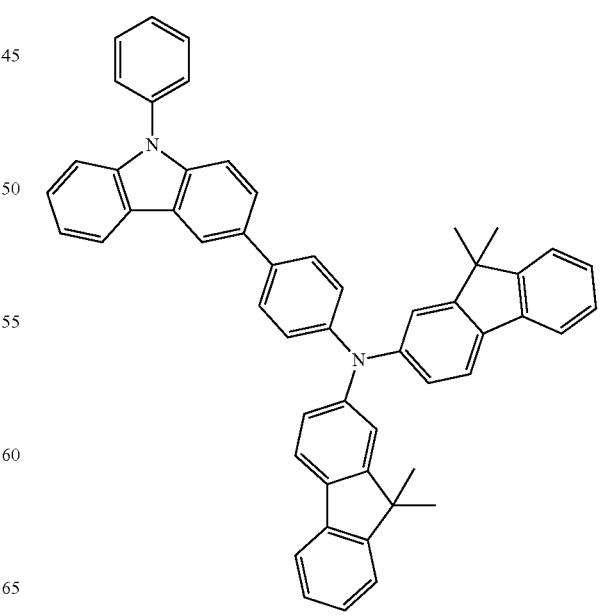

-continued

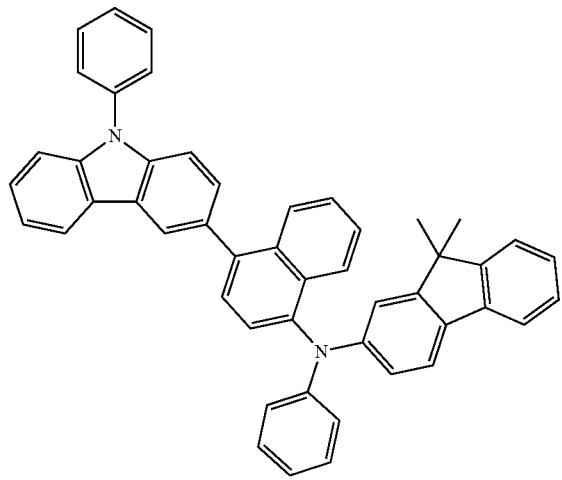
316

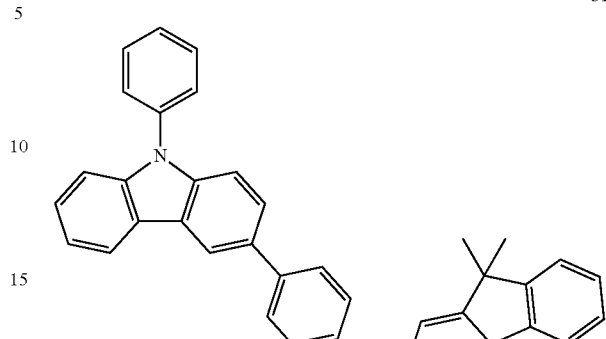
319

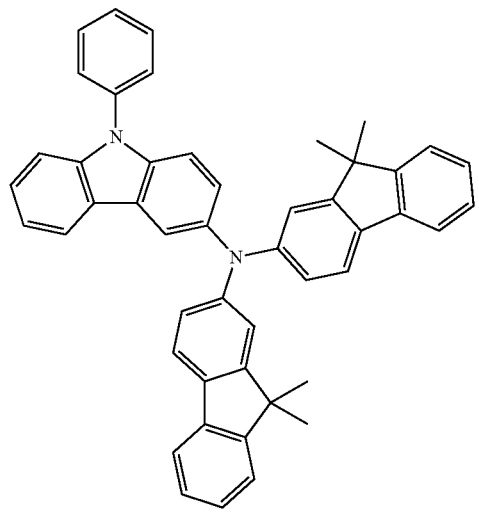
317

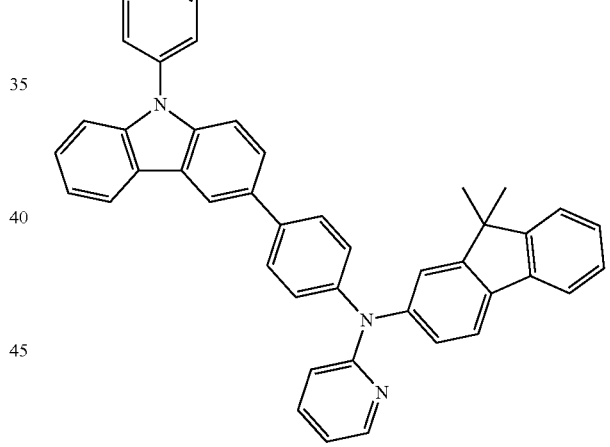
320

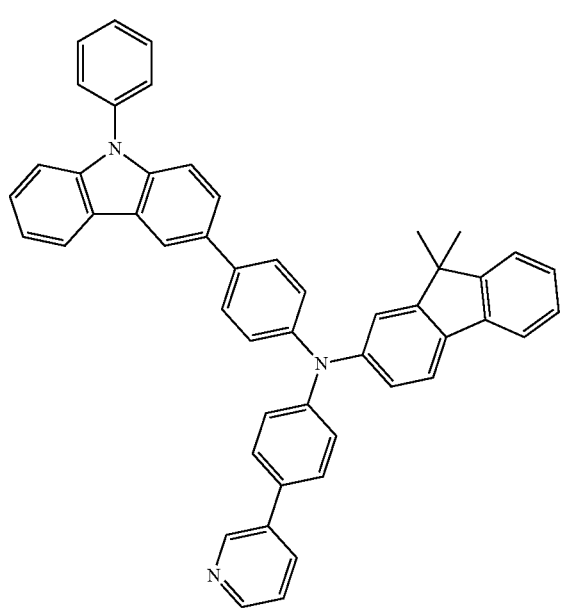
318

At least one of the hole injection layer, the hole transport layer, and the H-functional layer may further include a charge-generating material to improve layer conductivity, in addition to a suitable hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. For example, non-limiting examples of the p-dopant are quinine derivatives, such as tetracyanoquinodimethane (TCNQ) and 2,3,5,6-tetrafluoro-tetracyano-1,4-benzoquinodimethane(F4-TCNQ); metal oxide, such as tungsten oxide and molybdenym oxide; and a cyano group-containing compound, such as Compound 200 below, but is not limited thereto.

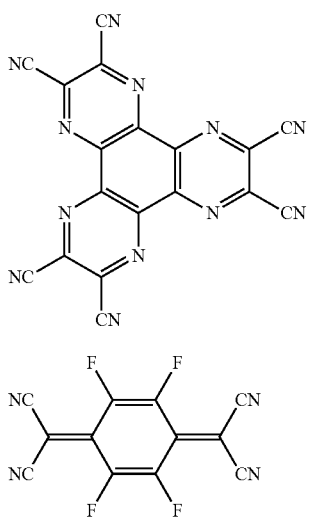

<Compound 200>

<F4-TCNQ>

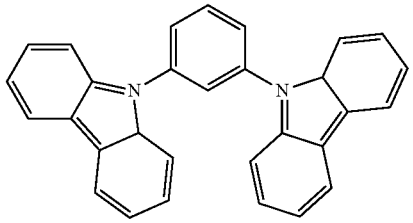

mCP

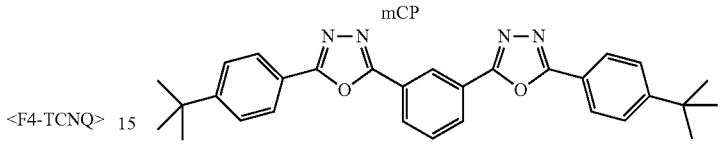

OXD-7

Also, a carbazole-based compound represented by Formula 10 below may be used.

<Formula 10>

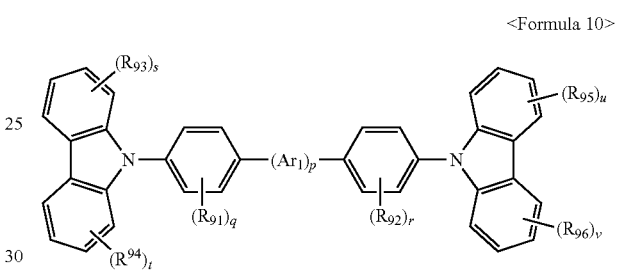

When the hole injection layer, hole transport layer, or H-functional layer further includes a charge-generating material, the charge-generating material may be homogeneously dispersed or non-homogeneously distributed in the layer.

A buffer layer may be disposed between at least one of the HIL, the HTL, and the H-functional layer, and the emission layer. The buffer layer may compensate for an optical resonance distance of light according to a wavelength of the light emitted from the emission layer, and thus may increase efficiency. The butter layer may include a suitable hole injecting material or hole transporting material. In some other embodiments, the buffer layer may include the same material as one of the materials included in the HIL, HTL, and H-functional layer that underlie the buffer layer.

Then, an emission layer (EML) may be formed on the HTL, the H-functional layer, or the buffer layer by vacuum deposition, spin coating, casting, LB deposition, or the like. When the EML is formed using vacuum deposition or spin coating, the deposition and coating conditions may be similar to those for the formation of the HIL, though the conditions for deposition and coating may vary according to the material that is used to form the EML.

The EML may include at least one of the organometallic complexes.

The organometallic complex included in the EML may act as a dopant (for example, blue phosphorescent dopant). In this regard, the EML may further include, in addition to the organometallic complex, a host.

The host may be at least one of a suitable host. As the host, Alq3, 4,4'-N,N'-dicarbazol-biphenyl (CBP), poly(n-vinylcarbazole) (PVK), 9,10-di(naphthalen-2-yl)anthracene (ADN), TCTA, 1,3,5-tris(N-phenylbenzimidazole2-yl)benzene (TPBI), 3-tert-butyl-9,10-di(naphth-2-yl) anthracene (TBADN), mCP, or OXD-7 may be used, but the host is not limited thereto.

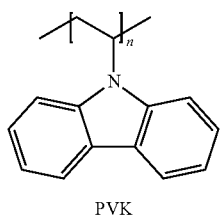

PVK

In Formula 10, $Ar_1$ may be a substituted or unsubstituted $C_1$-$C_{60}$ alkylene group, a substituted or unsubstituted $C_2$-$C_{60}$ alkenylene group, —C(=O)—, —N($R_{100}$)— (in which $R_{100}$ is a substituted or unsubstituted $C_6$-$C_{60}$ aryl group, or a substituted or unsubstituted $C_2$-$C_{60}$ heteroaryl group), a substituted or unsubstituted $C_6$-$C_{60}$ arylene group, or a substituted or unsubstituted $C_2$-$C_{60}$ heteroarylene group; p is an integer of 0 to 10; and $R_{91}$ to $R_{96}$ are each independently a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, or a substituted or unsubstituted $C_2$-$C_{60}$ heteroaryl group, and two neighboring substituents of $R_{91}$ to $R_{96}$ may be optionally linked to each other to form a substituted or unsubstituted $C_4$-$C_{20}$ alicyclic, a substituted or unsubstituted $C_2$-$C_{20}$ hetero alicyclic group, a substituted or unsubstituted $C_6$-$C_{20}$ aromatic ring, or a substituted or unsubstituted $C_2$-$C_{20}$ heteroaromatic ring; and q, r, s, t, u and v are each independently an integer of 1 to 4.

$Ar_1$ in Formula 10 may be a $C_1$-$C_5$ alkylene group, a $C_2$-$C_5$ alkenylene group, —C(=O)—, or —N($R_{100}$)—, wherein $R_{100}$ may be selected from:

a phenyl group, a naphthyl group, an anthryl group, a fluorenyl group, a carbazolyl group, a pyridinyl group, a pyrimidinyl group, and a triazinyl group; and a phenyl group, a naphthyl group, an anthryl group, a fluorenyl group, a carbazolyl group, a pyridinyl group, a pyrimidinyl group and a triazinyl group, each substituted with at least one selected from a deuterium atom, a halogen atom, a hydroxyl group, a cyano group, a nitro group, an amino group, a $C_1$-$C_{20}$ alkyl group, a $C_1$-$C_{20}$ alkoxy group, a phenyl group, a naphthyl group, an anthryl group, a fluorenyl group, a carbazolyl group, a pyridinyl group, a pyrimidinyl group, and a triazinyl group.

$R_{91}$ to $R_{96}$ in Formula 10 are each independently selected from:

a hydrogen atom, a deuterium atom, a halogen atom, a hydroxyl group, a cyano group, a nitro group, an amino group, an amidino group, hydrazine, hydrazone, a carboxyl group or a salt thereof, a sulfonic acid or a salt thereof, a phosphoric acid or a salt thereof, a $C_1$-$C_{20}$ alkyl group, and a $C_1$-$C_{20}$ alkoxy group; and a $C_1$-$C_{20}$ alkyl group and a $C_1$-$C_{20}$ alkoxy group, each substituted with at least one selected from a deuterium atom, a halogen atom, a hydroxyl group, a cyano group, a nitro group and an amino group.

The carbazole-based compound may be one of the following compounds, but is not limited thereto:

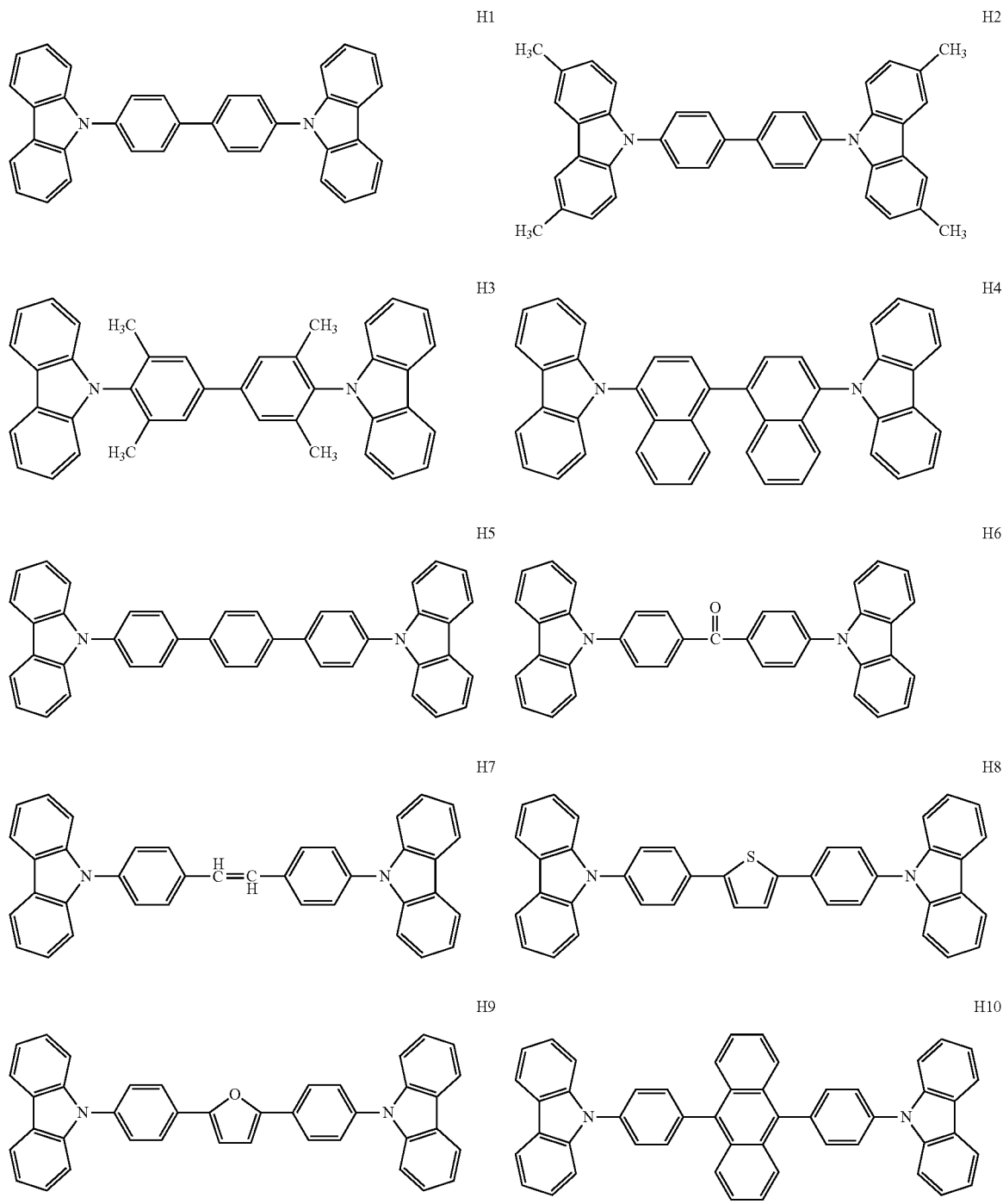

-continued
H11
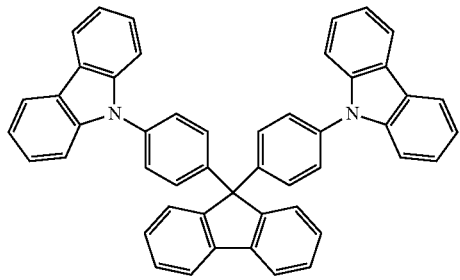
H12
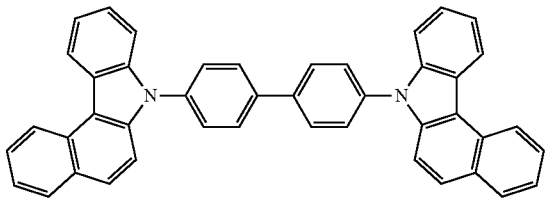
H13
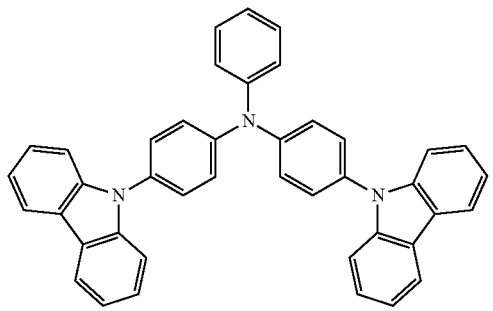
H14
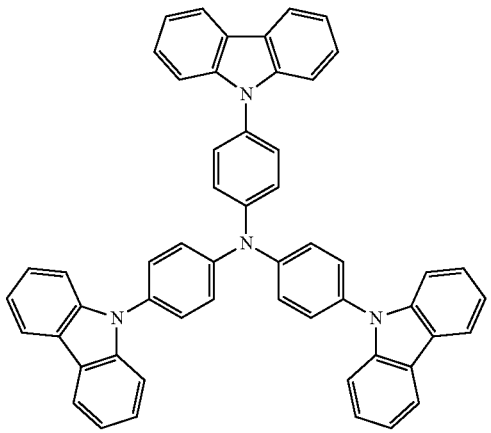
H15
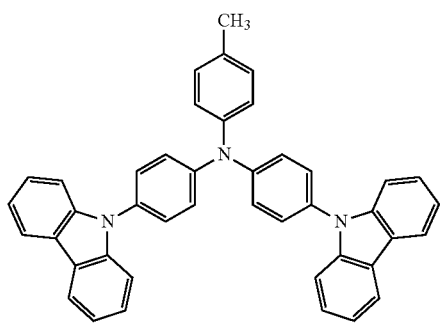
H16
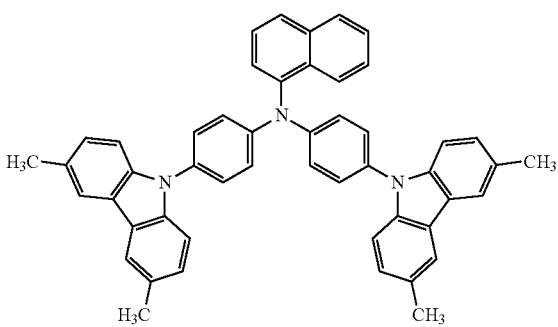
H17
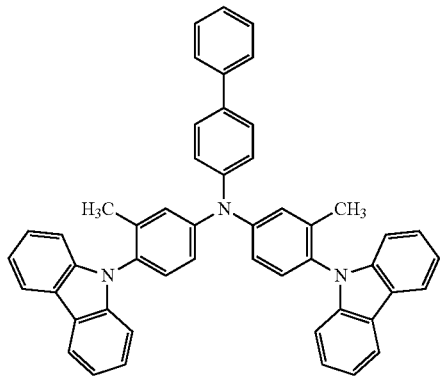
H18
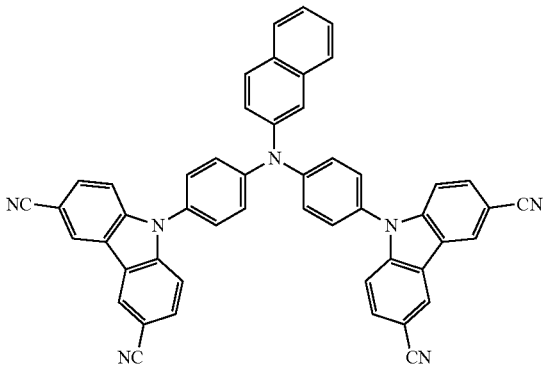

-continued
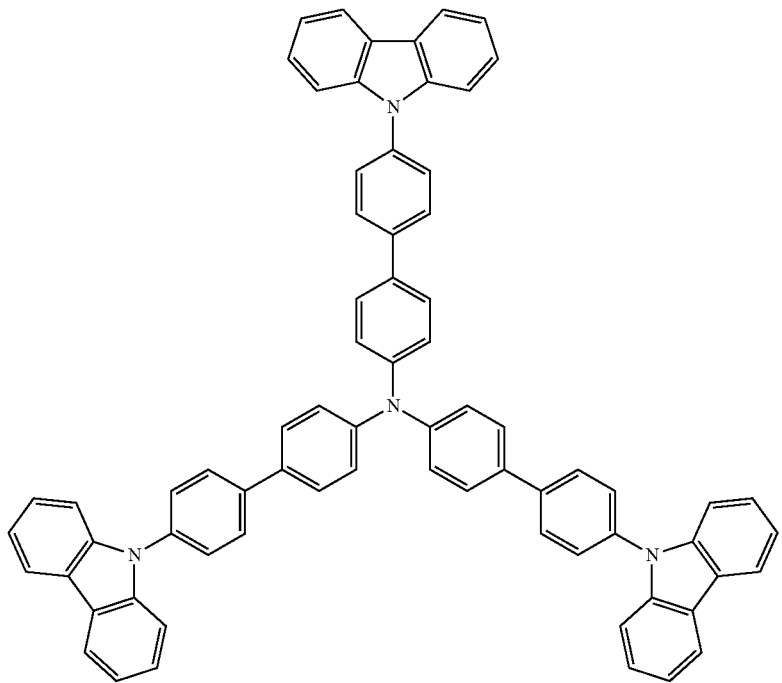
H19
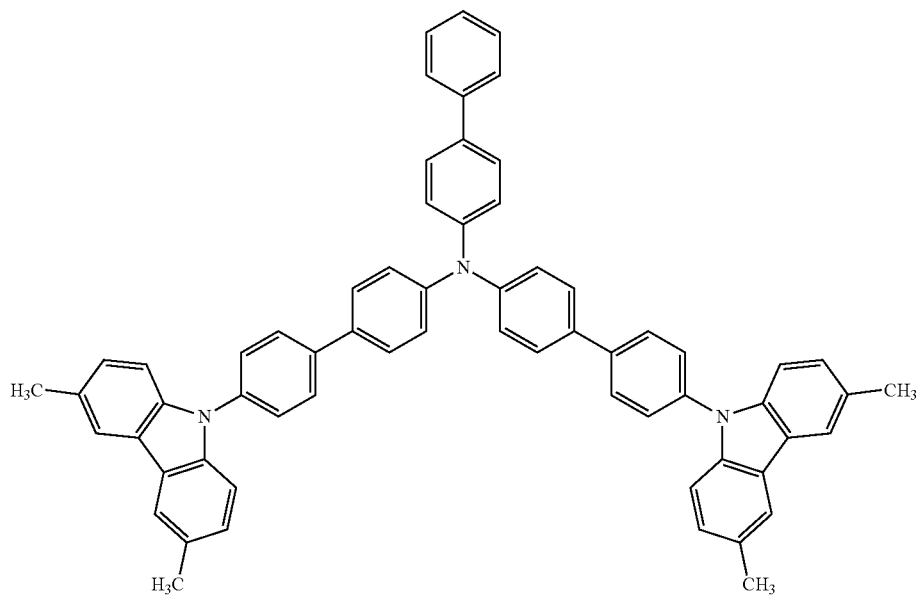
H20

H21
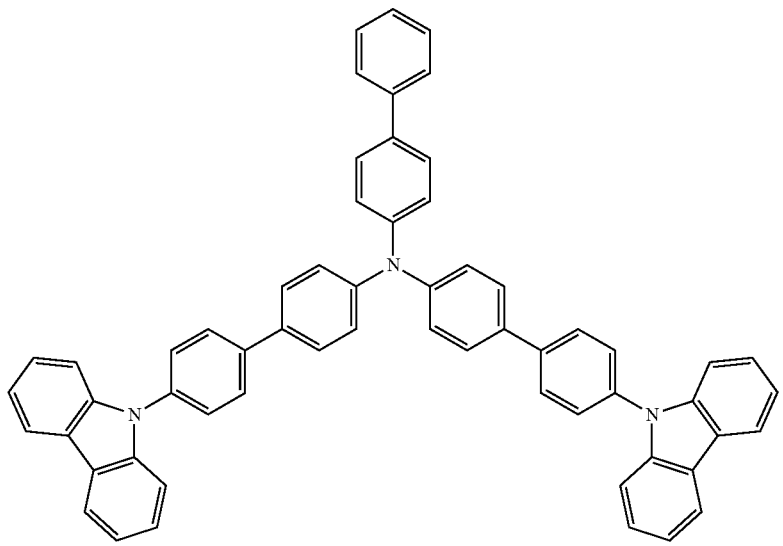
H22
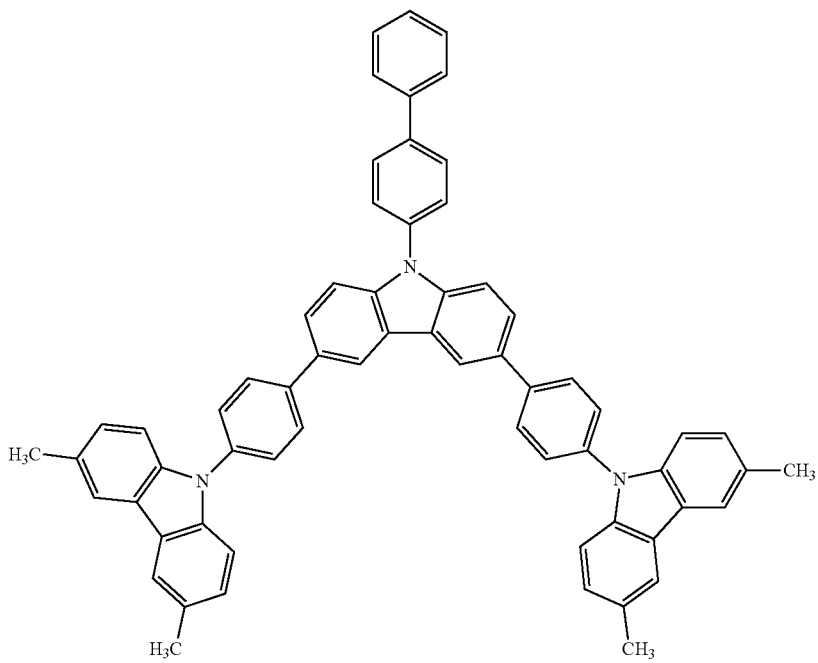
H23
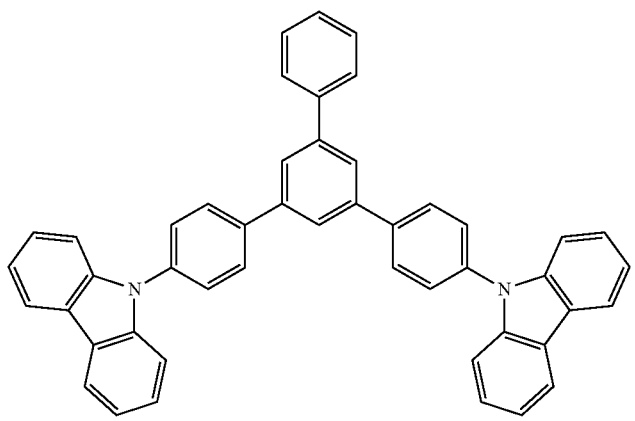

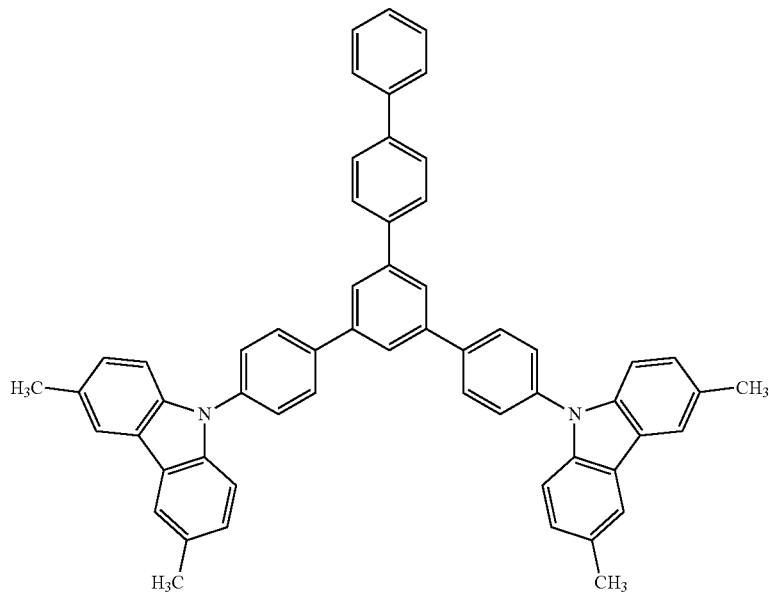
H24
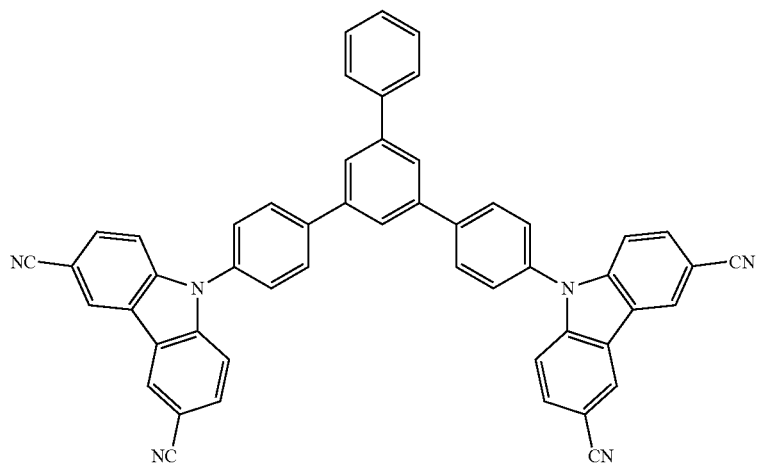
H25
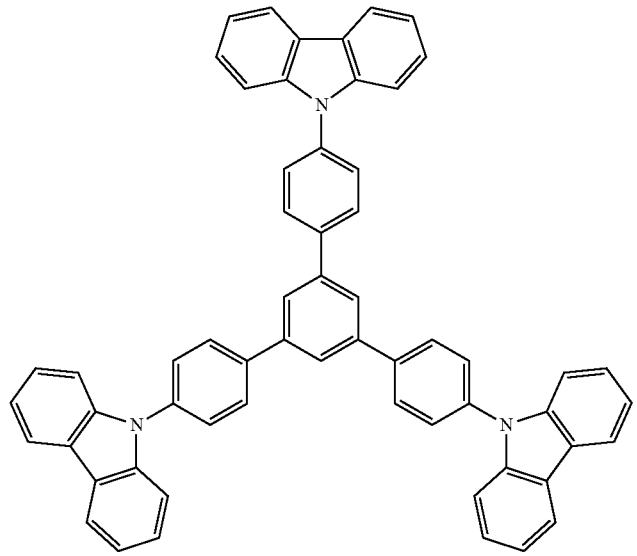
H26

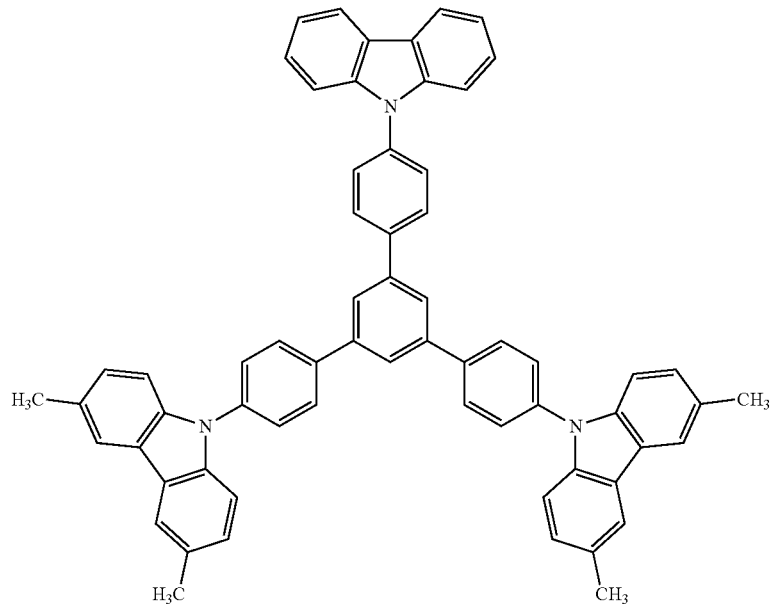
H27
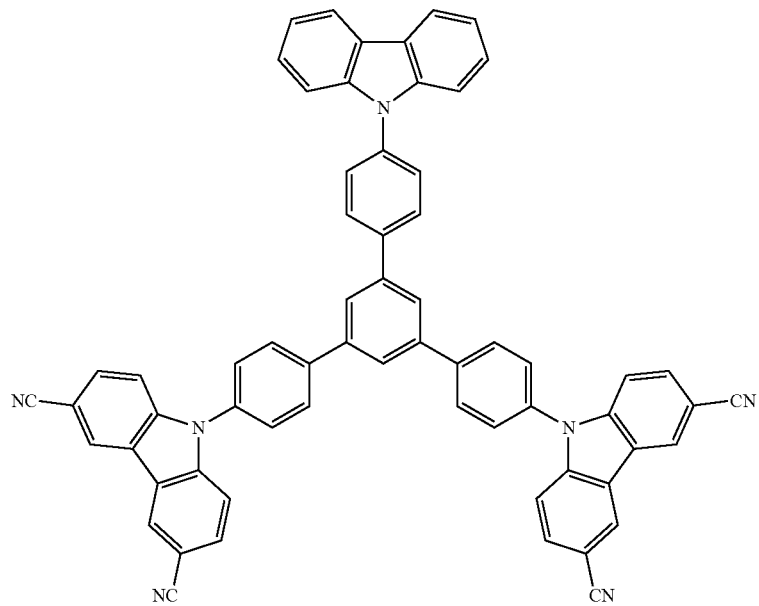
H28

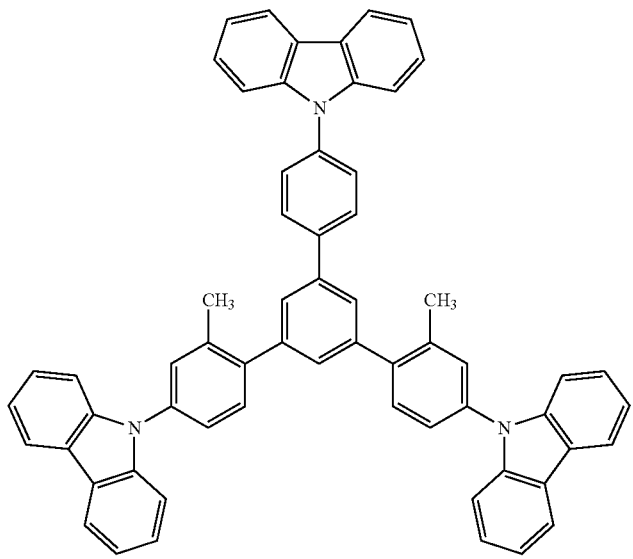

H29

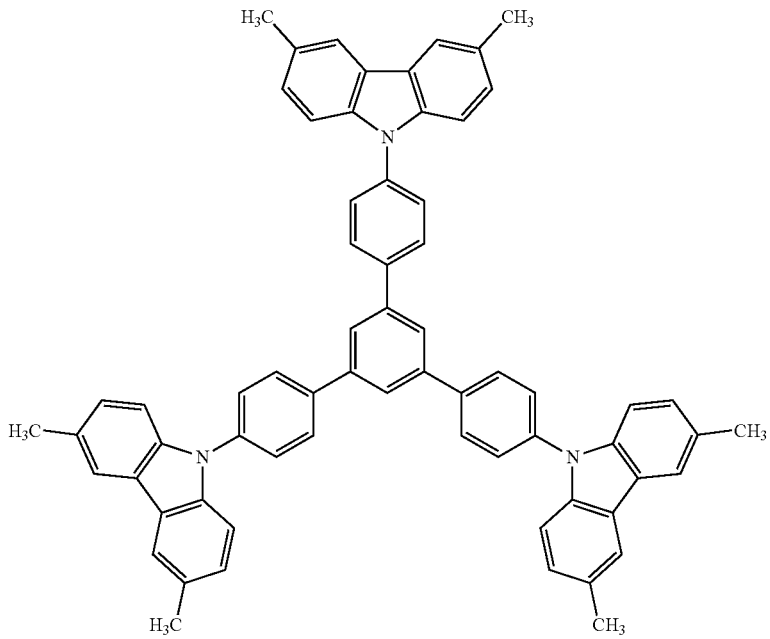

H30

When the emission layer includes a host and a dopant (that is, the organometallic complex represented by Formula 1), an amount of the dopant may be in a range of about 0.01 to about 15 wt % based on 100 wt % of the emission layer, but is not limited thereto.

A thickness of the emission layer may be in a range of about 200 Å to about 700 Å. When the thickness of the EML is within these ranges, the EML may have improved light emitting ability without a substantial increase in driving voltage.

Next, an electron transport layer (ETL) is formed on the EML using various methods, for example, by vacuum deposition, spin coating, casting, or the like. When the ETL is formed using vacuum deposition or spin coating, the deposition and coating conditions may be similar to those for the formation of the HIL, though the conditions for deposition and coating may vary according to the material that is used to form the ETL. As a material for an electron transport layer, suitable electron transportation materials that stably transport electrons injected from an electron injection electrode (cathode) may be used. Examples of suitable electron transportation materials are quinolin derivatives, in particular, tris(8-quinolate)aluminum($Alq_3$), TAZ, Balq, beryllium bis(benzoquinolin-10-olate) ($Bebq_2$), ADN, compound 101, compound 102, and Bphen, but are not limited thereto.

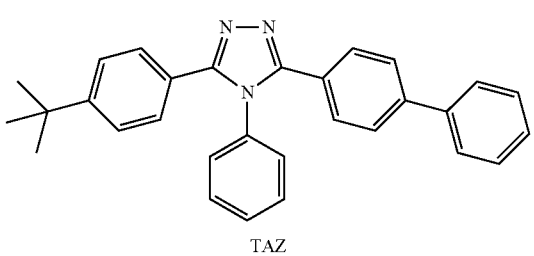

TAZ

-continued

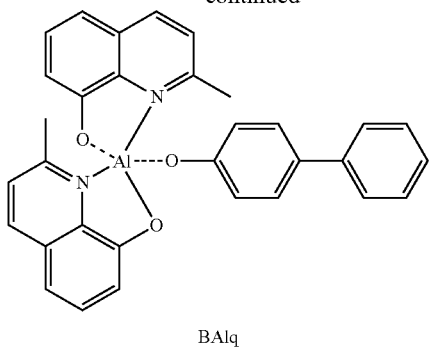

BAlq

<Compound 101>

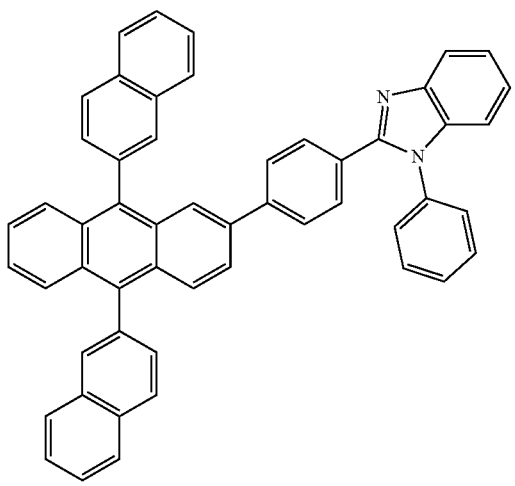

<Compound 102>

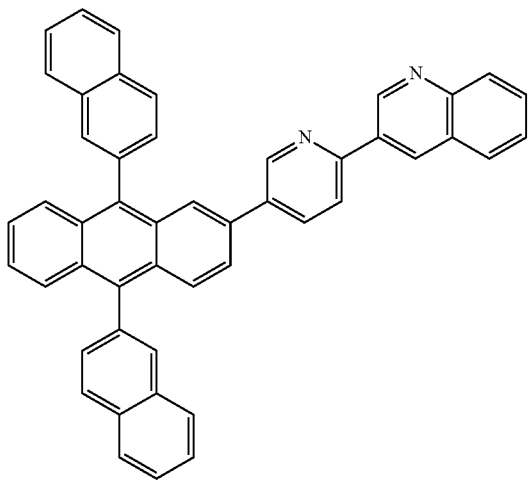

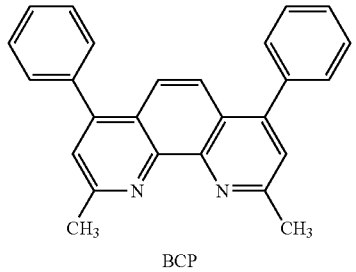

BCP

-continued

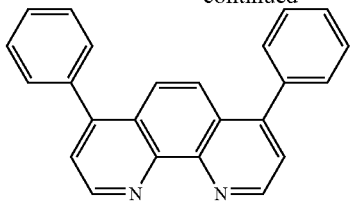

Bphen

A thickness of the ETL may be in a range of about 100 Å to about 1000 Å, for example, about 150 Å to about 500 Å. When the thickness of the ETL is within these ranges, the ETL may have satisfactory electron transporting ability without a substantial increase in driving voltage.

The ETL may further include, in addition to suitable electron transporting organic compounds, a metal-containing material.

The metal-containing material may include a lithium (Li) complex. Non-limiting examples of the Li complex are lithium quinolate (Liq) and Compound 203 below:

Compound 203

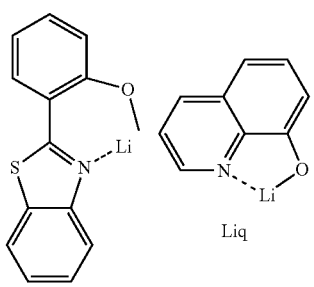

Liq

Then, an EIL, which facilitates injection of electrons from the second electrode, may be formed on the ETL. A suitable electron-injecting material may be used to form the EIL.

Non-limiting examples of materials for forming the EIL are LiF, NaCl, CsF, $Li_2O$, and BaO, which are suitable. Deposition conditions of the EIL may be similar to those for the formation of the HIL, although the conditions may vary according to a material that is used to form the EIL, in gene A thickness of the EIL may be in a range of about 1 Å to about 100 Å, or about 3 Å to about 90 Å. When the thickness of the EIL is within these ranges, the EIL may have satisfactory electron transporting ability without a substantial increase in driving voltage.

The second electrode 17 is disposed on the organic layer 15. The second electrode 17 may be a cathode, which is an electron injecting electrode. A metal for forming the second electrode may be a metal, an alloy, an electrically conductive compound, which have a low-work function, or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting diode, the transmission electrode may be formed of indium tin oxide (ITO) or indium zinc oxide (IZO).

An organic light-emitting diode 10 according to an example embodiment has been described with reference to FIG. 1, but is not limited to the structure illustrated in FIG. 1.

In addition, when the EML is formed using a phosphorescent dopant, to prevent diffusion of triplet excitons or holes toward the ETL, a hole blocking layer (HBL) may be formed between the HTL and the EML or between the H-functional layer and the EML by a method, for example, vacuum deposition, spin coating, casting, LB, or the like. When the HBL is formed using vacuum deposition or spin coating, the deposition and coating conditions may be similar to those for the formation of the HIL, though the conditions for deposition and coating may vary according to the material that is used to form the HBL. A suitable hole-blocking material may be used. Non-limiting examples of hole-blocking materials are oxadiazole derivatives, triazole derivatives, and phenanthroline derivatives. For example, BCP illustrated below may be used as a material for the HBL.

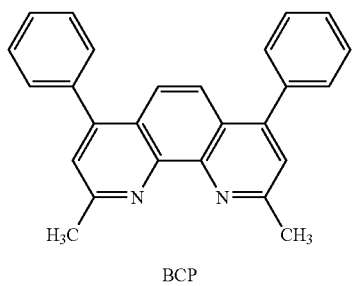 [SMILES: Cc1cc(-c2ccccc2)c2ccc3c(-c4ccccc4)cc(C)nc3c2n1 ; "BCP"]

BCP

A thickness of the HBL may be in a range of about 20 Å to about 1000 Å, for example, about 30 Å to about 300 Å. When the thickness of the HBL is within these ranges, the HBL may have improved hole blocking ability without a substantial increase in driving voltage.

The unsubstituted $C_1$-$C_{60}$ alkyl group (or $C_1$-$C_{60}$ alkyl group) used herein may be a $C_1$-$C_{60}$ linear or branched alkyl group, such as methyl, ethyl, propyl, isobutyl, sec-butyl, pentyl, iso-amyl, or hexyl, and the substituted $C_1$-$C_{60}$ alkyl group is obtained by substituting at least one substituent of the substituted $C_1$-$C_{60}$ alkyl group with one selected from:

a deuterium atom; —F; —Cl; —Br; —I; —CN; hydroxyl group; —NO$_2$; an amino group, an amidino group, hydrazine, hydrazone, a carboxyl group or a salt thereof, a sulfonic acid or a salt thereof, a phosphoric acid or a salt thereof; tri($C_6$-$C_{60}$ aryl)silyl group;

a $C_1$-$C_{60}$ alkyl group, a $C_1$-$C_{60}$ alkoxy group, a $C_2$-$C_{60}$ alkenyl group, and a $C_2$-$C_{60}$ alkynyl group;

a $C_1$-$C_{60}$ alkyl group, a $C_1$-$C_{60}$ alkoxy group, a $C_2$-$C_{60}$ alkenyl group, and a $C_2$-$C_{60}$ alkynyl group, each substituted with at least one selected from a deuterium atom, —F, —Cl, —Br, —I, —CN, a hydroxyl group, —NO$_2$, an amino group, amidino group, hydrazine, hydrazone, a carboxyl group or a salt thereof, a sulfonic acid or a salt thereof, and a phosphoric acid or a salt thereof;

a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group and a $C_6$-$C_{60}$ arylthio group; and a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group, each substituted with at least one selected from a deuterium atom, —F, —Cl, —Br, —I, —CN, a hydroxyl group, —NO$_2$, an amino group, an amidino group, hydrazine, hydrazone, a carboxyl group or a salt thereof, a sulfonic acid or a salt thereof, a phosphoric acid or a salt thereof, a $C_1$-$C_{60}$ alkyl group, a $C_1$-$C_{60}$ alkyl group, a $C_1$-$C_{60}$ alkoxy group, a $C_2$-$C_{60}$ alkenyl group, a $C_2$-$C_{60}$ alkynyl group, a $C_6$-$C_{60}$ aryl group, and a $C_2$-$C_{60}$ heteroaryl group, each substituted with at least one F.

The unsubstituted $C_1$-$C_{60}$ alkoxy group (or $C_1$-$C_{60}$ alkoxy group) used herein has a formula of —OA (where A is the unsubstituted $C_1$-$C_{60}$ alkyl group described above), and detailed examples thereof are methoxy, ethoxy, and isopropyloxy, and at least one hydrogen atom of these alkoxy groups may be substituted with the same substituent as described above in connection with the substituted $C_1$-$C_{60}$ alkyl group.

The unsubstituted $C_2$-$C_{60}$ alkenyl group (or $C_2$-$C_{60}$ alkenyl group) used herein refers to an unsubstituted $C_2$-$C_{60}$ alkyl group having one or more carbon double bonds at a center or end thereof. Examples of the unsubstituted $C_2$-$C_{60}$ alkenyl group are ethenyl, propenyl, and butenyl. At least one hydrogen atom of these unsubstituted $C_2$-$C_{60}$ alkenyl groups may be substituted with the same substituent as described above in connection with the substituted $C_1$-$C_{60}$ alkyl group.

The unsubstituted $C_2$-$C_{60}$ alkenyl group (or $C_2$-$C_{60}$ alkenyl group) used herein refers to an unsubstituted $C_2$-$C_{60}$ alkyl group having one or more carbon double bonds at a center or end thereof. Examples of the unsubstituted $C_2$-$C_{60}$ alkenyl group are ethenyl, propenyl, and butenyl. At least one hydrogen atom of these unsubstituted $C_2$-$C_{60}$ alkenyl groups may be substituted with the same substituent as described above in connection with the substituted $C_1$-$C_{60}$ alkyl group.

The unsubstituted $C_3$-$C_{60}$ cycloalkyl group used herein refers to a monovalent $C_3$ to $C_{60}$ cyclic saturated, and examples thereof are cyclopropyl, cyclobutyl, cyclopentyl, cyclohexyl, and cycloctyl. At least one hydrogen atom of these cycloalkyl groups may be substituted with the same substituent as described above in connection with the substituted $C_1$-$C_{60}$ alkyl group.

The unsubstituted $C_3$-$C_{60}$ cycloalkenyl group used herein refers to an unsaturated hydrocarbon group having one or more carbon double bonds and being a ring-type group, not an aromatic ring, and examples thereof are cyclopropenyl, cyclobutenyl, cyclopentenyl, cyclohexenyl, cycloheptenyl, a 1,3-cyclohexadienyl group, a 1,4-cyclohexadienyl group, a 2,4-cycloheptadienyl group, and a 1,5-cyclooctadienyl group. At least one hydrogen atom of these cycloalkenyl groups may be substituted with the same substituent as described above in connection with the substituted $C_1$-$C_{60}$ alkyl group.

The unsubstituted $C_6$-$C_{60}$ aryl group used herein is a monovalent group having a carbocyclic aromatic system having 6 to 60 carbon atoms including at least one aromatic ring. The unsubstituted $C_6$-$C_{60}$ arylene group is a divalent group having a carbocyclic aromatic system having 6 to 60 carbon atoms including at least one aromatic ring. When the aryl group and the arylene group include two or more rings, the rings may be fused to each other. At least one hydrogen atom of these aryl groups and arylene groups may be substituted with the same substituent as described above in connection with the substituted $C_1$-$C_{60}$ alkyl group.

Examples of the substituted or unsubstituted $C_6$-$C_{60}$ aryl group are a phenyl group, a $C_1$-$C_{10}$ alkylphenyl group (for example, ethylphenyl group), a $C_1$-$C_{10}$ alkylbiphenyl group (for example, ethylbiphenyl group), a halophenyl group (for example, an o-, m- or p-fluorophenyl group, a dichlorophenyl group), a dicyanophenyl group, a trifluoromethoxyphenyl group, o-, m-, and p-tolyl groups, o-, m- and p-cumenyl groups, a mesityl group, a phenoxyphenyl group, a (α,α- dimethylbenzene)phenyl group, a (N,N'-dimethyl)aminophenyl group, a (N,N'-diphenyl)aminophenyl group, a pentalenyl group, an indenyl group, a naphthyl group, halonaphthyl group (for example, a fluoronaphthyl group), a $C_1$-$C_{10}$ alkylnaphthyl group (for example, a methylnaphthyl group), a $C_1$-$C_{10}$ alkoxynaphthyl group (for example, a methoxynaphthyl group), an anthracenyl group, azrenyl group, a heptalenyl group, an acenaphthylenyl group, a phenalenyl group, a fluorenyl group, anthraquinolinyl group, a methylanthryl group, a phenanthryl group, a triphenylenyl group, a pyrenyl group, a chrysenyl group, an ethyl-chrysenyl group, a picenyl group, perylenyl group, a chloroperylenyl group, a pentaphenyl group, a pentasenyl group, a tetraphenylenyl group, a hexaphenyl group, a hexacenyl group, a rubicenyl group, a coroneryl group, a trinaphthylenyl group, a heptaphenyl group, a heptacenyl group, a piranthrenyl group, and an obarenyl group, and examples of the substituted $C_6$-$C_{60}$ aryl group may be easily understood by referring to the examples of the unsubstituted $C_6$-$C_{60}$ aryl group and the substituents of the substituted $C_1$-$C_{60}$ alkyl group. Examples of the substituted or unsubstituted $C_6$-$C_{60}$ arylene group may be easily understood by referring to examples of the substituted or unsubstituted $C_6$-$C_{60}$ aryl group.

The unsubstituted $C_2$-$C_{60}$ heteroaryl group used herein refers to a monovalent group having a system composed of one or more aromatic rings having at least one hetero atom selected from nitrogen (N), oxygen (O), phosphorous (P), and sulfur (S) as a ring-forming element, and carbon atoms as the remaining ring atoms. The unsubstituted $C_2$-$C_{60}$ heteroarylene group used herein refers to a divalent group having a system composed of one or more aromatic rings having at least one hetero atom selected from nitrogen (N), oxygen (O), phosphorous (P), and sulfur (S) and carbon atoms as the remaining ring atoms. In this regard, when the heteroaryl group and the heteroarylene group each include two or more rings, the rings may be fused to each other. At least one hydrogen atom of the heteroaryl group and the heteroarylene group may be substituted with the same substituent described in connection with the $C_1$-$C_{60}$ alkyl group.

Examples of the unsubstituted $C_2$-$C_{60}$ heteroaryl group are a pyrazolyl group, an imidazolyl group, a oxazolyl group, a thiazolyl group, a triazolyl group, tetrazolyl, an oxadiazolyl group, a pyridinyl group, a pyridazinyl group, a pyrimidinyl group, a triazinyl group, a carbazolyl group, an indolyl group, a quinolinyl group, an isoquinolinyl group, benzoan imidazolyl group, an imidazo pyridinyl group, and an imidazo pyrimidinyl group. Examples of the unsubstituted $C_2$-$C_{60}$ heteroarylene group may be easily understood by referring to the examples of the substituted or unsubstituted $C_2$-$C_{60}$ arylene group.

The substituted or unsubstituted $C_6$-$C_{60}$ aryloxy group indicates —$OA_2$ (where $A_2$ is the substituted or unsubstituted $C_6$-$C_{60}$ aryl group), and the substituted or unsubstituted $C_5$-$C_{60}$ arylthio group indicates —$SA_3$ (where $A_3$ is the substituted or unsubstituted $C_6$-$C_{60}$ aryl group).

Hereinafter, an organic light-emitting diode according to an example embodiment is described in detail with reference to Synthesis Examples and Examples. However, the organic light-emitting diode according to an example embodiment is not limited to the Synthesis Examples and Examples.

An organic light-emitting diode including the organometallic complex has high efficiency and high color purity. Accordingly, when the organometallic complex is used, a high-quality organic light-emitting diode may be embodied.

EXAMPLE

Synthesis Example 1

Synthesis of Complex 1

Synthesis of Intermediate 1(1)

Intermediate 1(1) was synthesized according to Reaction Scheme 1(1) below:

<Reaction Scheme 1(1)>

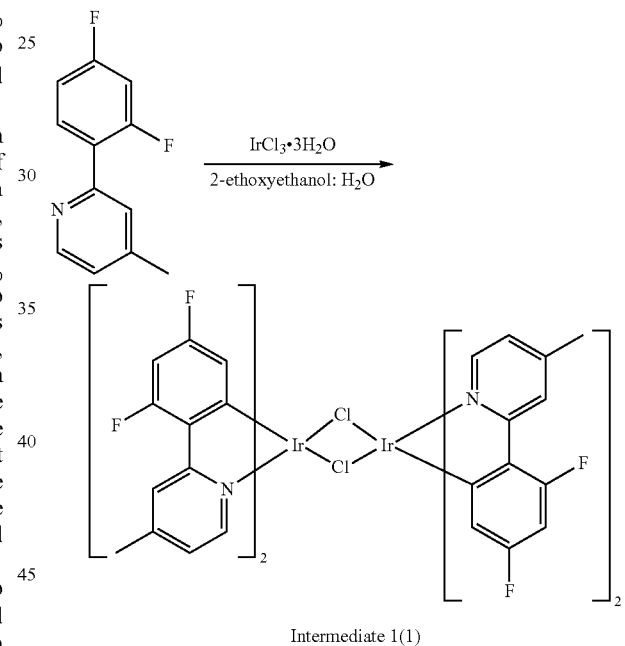

Intermediate 1(1)

3.6 g (17.3 mmol) of 2-(2,4-difluorophenyl)-4-methylpyridine was dissolved in 45 mL of 2-ethoxyethanol, and 2.4 g (7.6 mmol) of iridium chloride hydrate and 15 mL of distilled water were added thereto and the mixture was stirred at a temperature of 130° C. for 20 hours. After the reaction was finished, the reaction solution was cooled to room temperature and filtered to obtain a precipitate, and the precipitate was washed with methanol, and dried in a vacuum condition to obtain Intermediate 1(1) (4.3 g, Yield: 60%).

Synthesis of Complex 1

Complex 1 was synthesized according to Reaction Scheme 1(2) below:

<Reaction Scheme 1(2)>

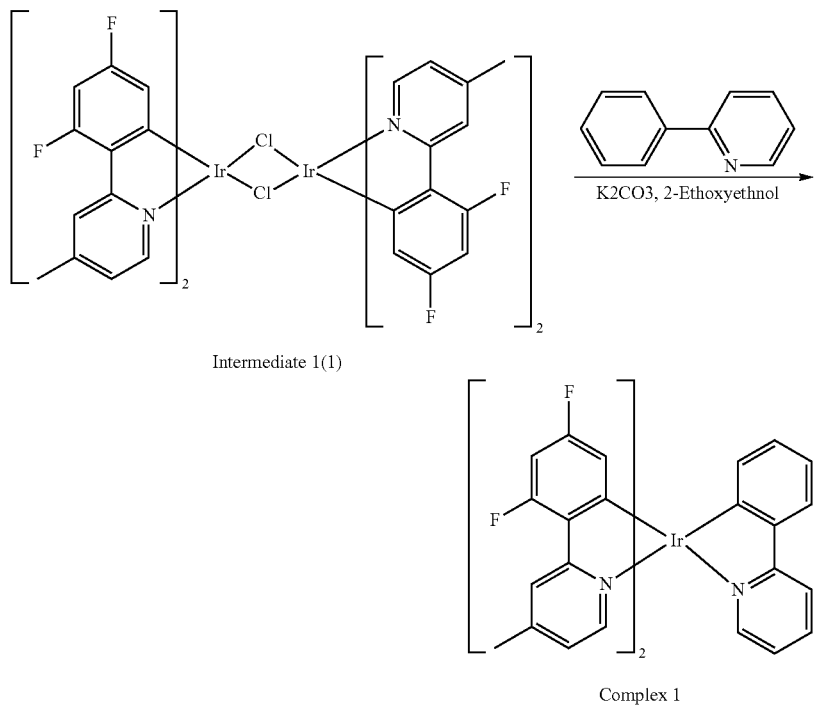

Intermediate 1(1)

Complex 1

1.0 g (1.03 mmol) of Intermediate 1(1), 0.38 g (2.44 mmol) of phenylpyridine, and 0.34 g (2.46 mmol) of K$_2$CO$_3$ were added to 30 mL of 2-ethoxyethanol, and the mixture was stirred at a temperature of 130° C. for 12 hours. After the reaction was finished, the reaction solution was cooled to room temperature and filtered to obtain a precipitate, and the precipitate was washed with methanol. The obtained precipitate was dissolved in dichloromethane and filtered through a short pad, and the filtered dichloromethane solution was boiled, and methanol was added in a small amount thereto to precipitate Complex 1 (0.60 g, Yield: 53%).

$^1$H-NMR: 8.56 (3H), 8.30 (1H), 7.97 (3H), 7.53 (4H), 7.00 (7H), 2.36 (6H). APCI-MS (m/z): 755[M+]

Synthesis Example 2

Synthesis of Complex 2

Synthesis of Intermediate 2(1)

Intermediate 2(1) was synthesized according to Reaction Scheme 2(1) below:

<Reaction Scheme 2(1)>

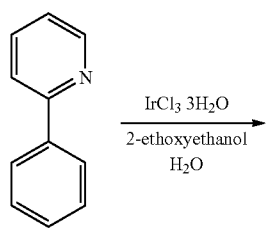

-continued

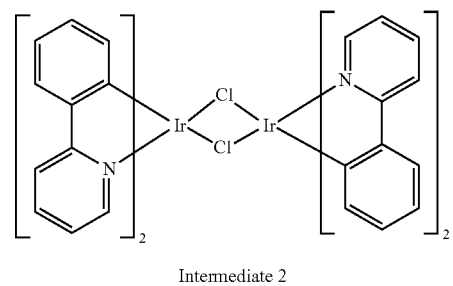

Intermediate 2

2.7 g (17.3 mmol) of 2-phenylpyridine was dissolved in 45 mL of 2-ethoxyethanol, and 2.4 g (7.6 mmol) of iridium chloride hydrate and 15 mL of distilled water were added thereto and the mixture was stirred at a temperature of 130° C. for 20 hours. After the reaction was finished, the reaction solution was cooled to room temperature and filtered to obtain a precipitate, and the precipitate was washed with methanol, and dried in a vacuum condition to obtain Intermediate 1(1) (4.0 g, Yield: 60%).

Synthesis of Complex 2

Complex 2 was synthesized according to Reaction Scheme 2(2) below:

<Reaction Scheme 2(2)>

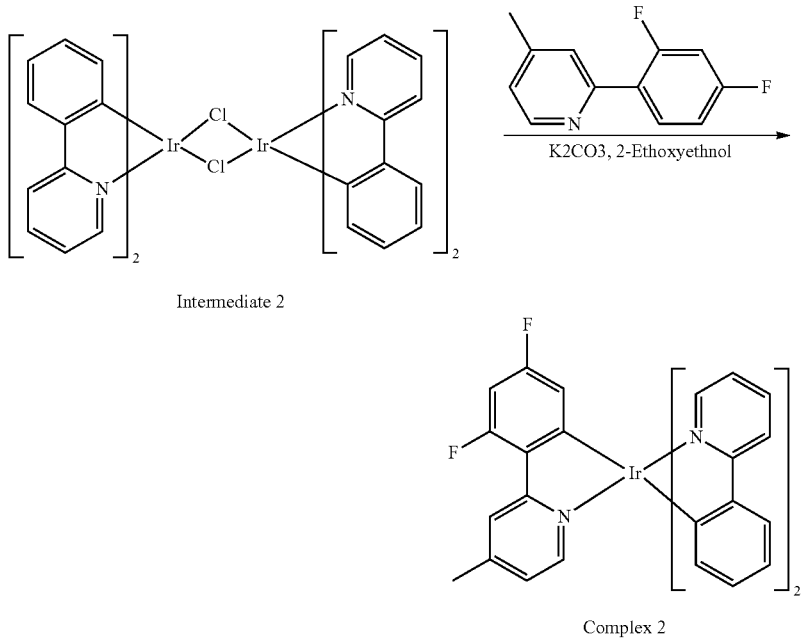

Intermediate 2

Complex 2

0.84 g (1.03 mmol) of Intermediate 1(1), 0.5 g (2.44 mmol) of 2-(2,4-difluorophenyl)-4-methylpyridine, and 0.34 g (2.46 mmol) of $K_2CO_3$ were added to 30 mL of 2-ethoxyethanol, and then the mixture was stirred at a temperature of 130° C. for 12 hours. After the reaction was finished, the reaction solution was cooled to room temperature and filtered to obtain a precipitate, and the precipitate was washed with methanol. The obtained precipitate was dissolved in dichloromethane and filtered through a short pad, and the filtered dichloromethane solution was boiled, and methanol was added in a small amount thereto to precipitate Complex 1 (0.57 g, Yield: 50%).

$^1$H-NMR: 8.57 (3H), 8.29 (3H), 7.80 (3H), 7.54 (8H), 6.98 (5H), 2.36 (6H). APCI-MS (m/z): 705[M+]

Evaluation Example 1

Luminescent Characteristics of Complex 1

Figure 2:
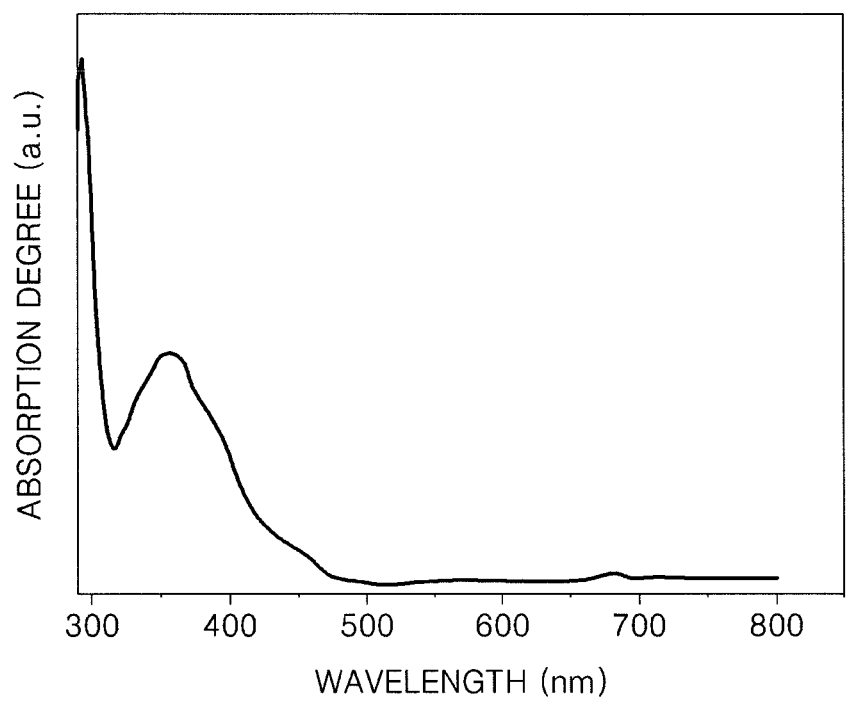
FIG. 2 shows an ultraviolet (UV) absorption spectrum of Complex 1 in solution.

The UV absorption spectrum and photoluminescence (PL) spectrum of Complex 1 synthesized in Synthesis Example 1 were evaluated to identify luminescent characteristics of Complex 1. First, Complex 1 was diluted in toluene to a concentration of 0.2 mM, and UV absorption spectrum of Complex 1 in solution was measured by using Shimadzu UV-350 Spectrometer. Results thereof are shown in FIG. 2. Also, Complex 1 was diluted in toluene to a concentration of 10 mM, and PL spectrum of Complex 1 in solution was measured by using ISC PC1 spectrofluorometer equipped with a Xenon lamp, and results thereof are shown in FIG. 3.

Figure 3:
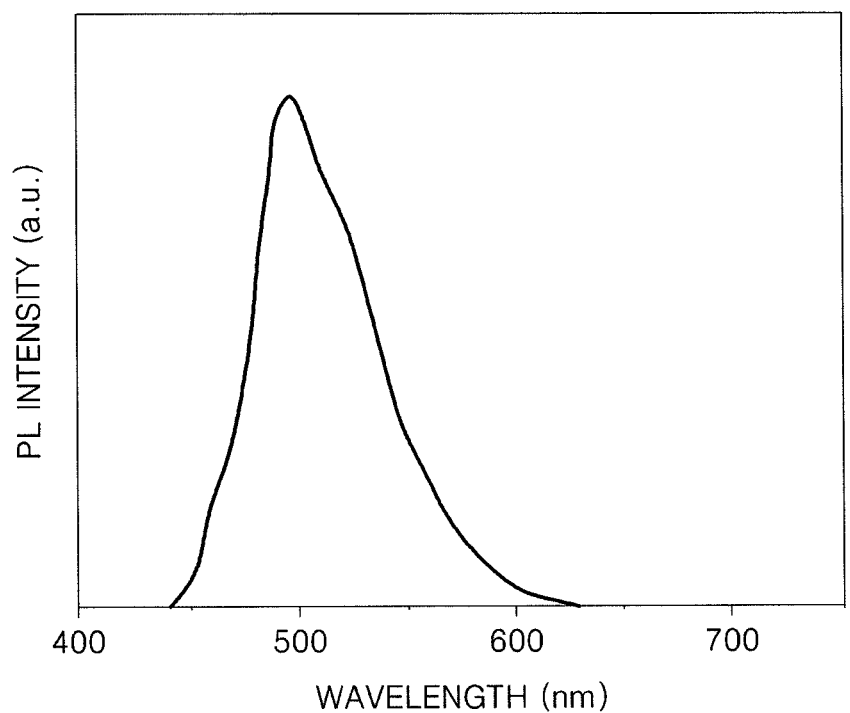
FIG. 3 is a PL spectrum of Complex 1 in solution.

Referring to FIGS. 2 and 3, it was confirmed that Complex 1 has excellent UV absorption characteristics and PL luminescent characteristics.

Evaluation Example 2

Thermal Stability of Complex 1

Thermal stability of Complex 1 was evaluated by measuring Tg (glass transition temperature) and Tm (melting point) of Complex 1. Tg and Tm were measured by performing thermal analysis (N2 atmosphere, temperature sections: room temperature to 600° C. (10° C./min)-TGA, and from room temperature to 400° C.-DSC, Pan Type: Pt Pan in disposable Al Pan(TGA), and disposable Al pan(DSC)) using thermo gravimetric analysis (TGA) and differential scanning calorimetry (DSC). TGA data of Complex 1 is shown in FIG. 4.

Figure 4:
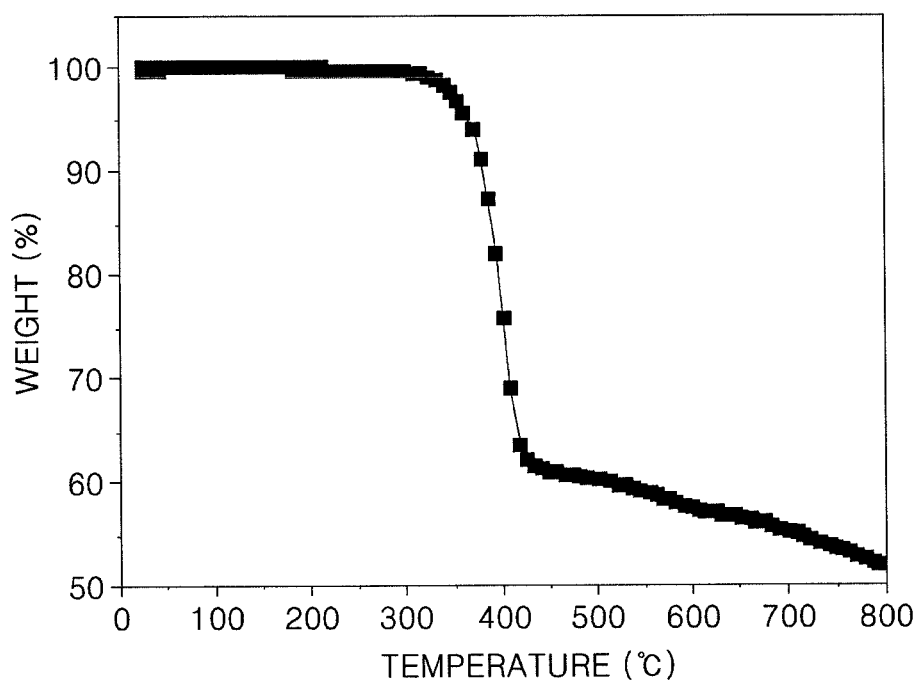
FIG. 4 shows TGA data of Complex 1.

From FIG. 4, it was confirmed that Complex 1 has excellent thermal stability.

Evaluation Example 3

Electric Characteristics of Complex 1

Electric characteristics of Complex 1 were identified by evaluating electric characteristics thereof using cyclic voltammetry (CV) (electrolyte: 0.1M $Bu_4NClO_4$/solvent: $CH_2Cl_2$/electrode: 3 electrode system (working electrode: GC, reference electrode: Ag/AgCl, and an auxiliary electrode: Pt)), and results thereof are shown in FIG. 5.

Figure 5:
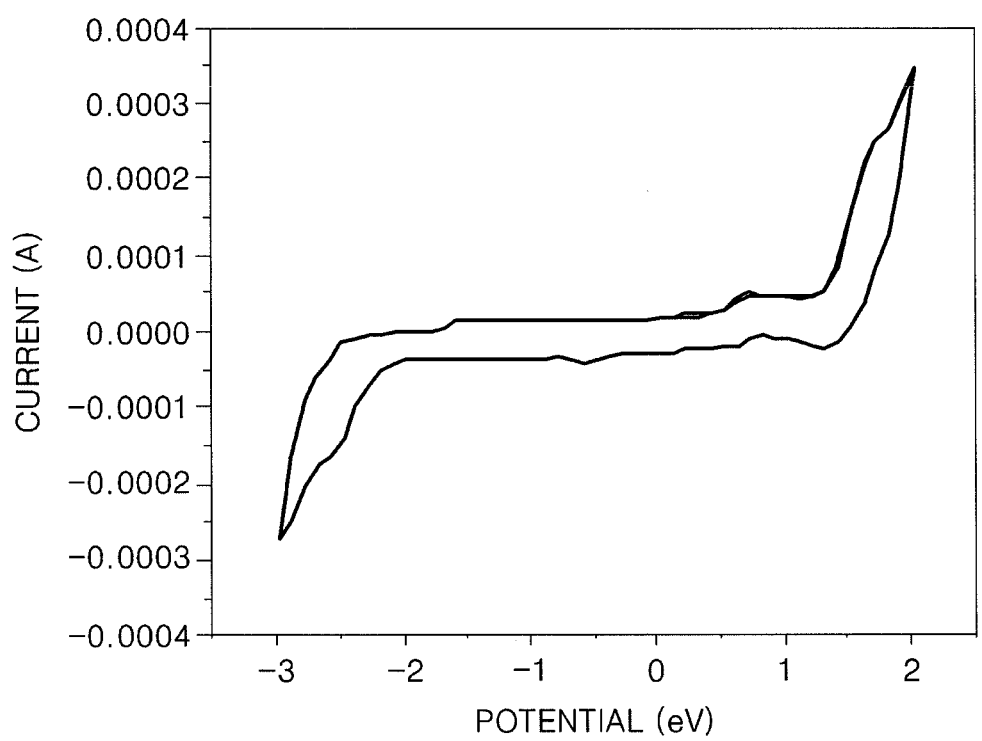
FIG. 5 shows CV data of Complex 1.

From FIG. 5, it was confirmed that Complex 1 has an electric characteristics suitable for use as a compound for an organic light-emitting diode.

Evaluation Example 4

Luminescent Characteristics of Complex 2

The UV absorption spectrum and photoluminescence (PL) spectrum of Complex 2 synthesized in Synthesis Example 2 were evaluated to identify luminescent characteristics of Complex 2. First, Complex 2 was diluted in toluene to a concentration of 0.2 mM, and UV absorption spectrum of Complex 2 in solution was measured by using Shimadzu UV-350 Spectrometer. Results thereof are shown in FIG. 2. Also, Complex 2 was diluted in toluene to a concentration of 10 mM, and PL spectrum of Complex 1 in solution was measured by using ISC PC1 spectrofluorometer equipped with a Xenon lamp, and results thereof are shown in FIG. 7.

Figure 6:
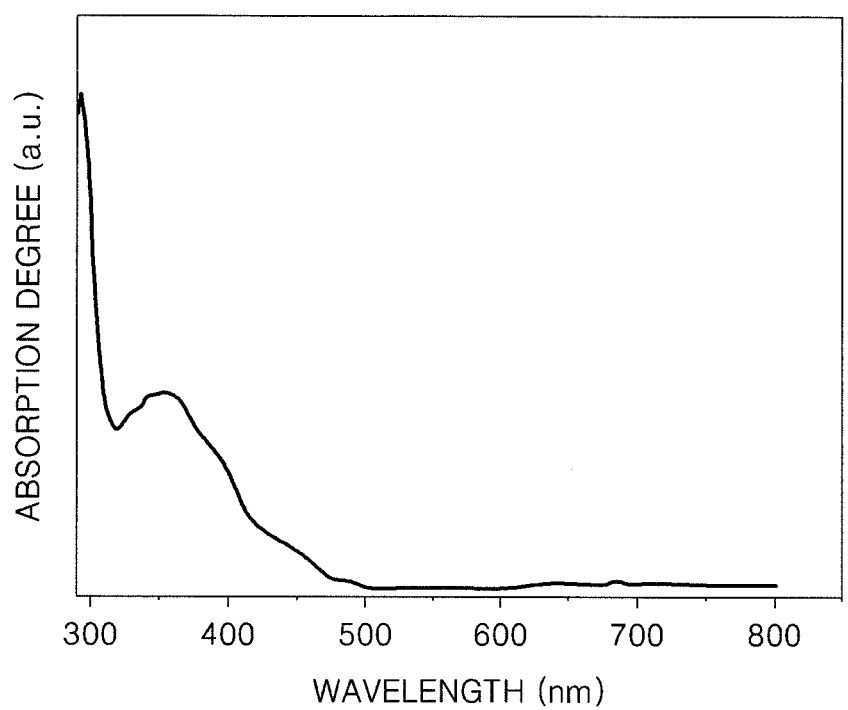
FIG. 6 shows a UV absorption of spectrum of complex 2 in solution.
Figure 7:
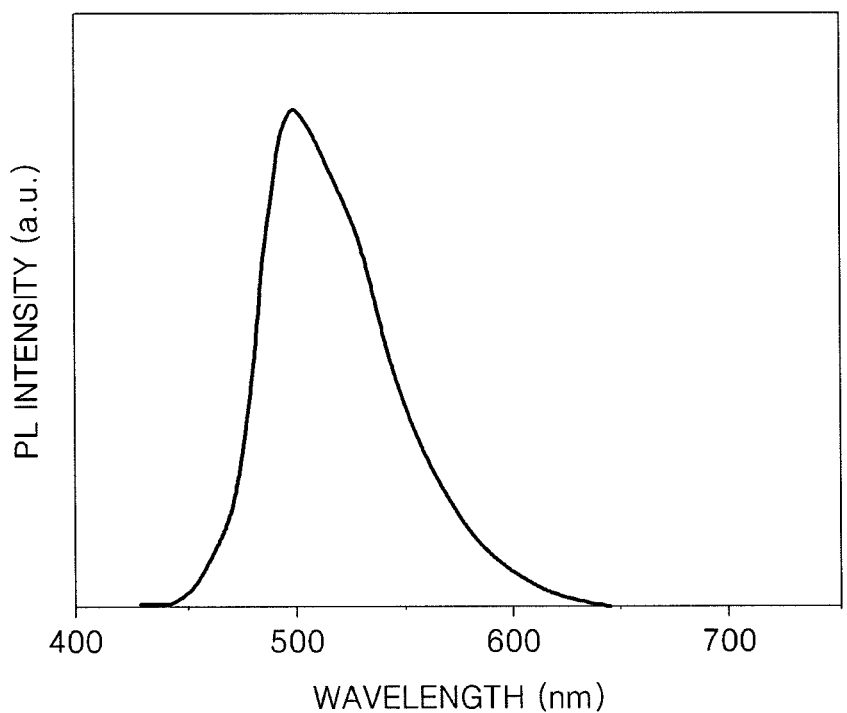
FIG. 7 is a PL spectrum of complex 2 in solution.

Referring to FIGS. 6 and 7, it was confirmed that Complex 2 has excellent UV absorption characteristics and PL luminescent characteristics.

Evaluation Example 5

Thermal Stability of Complex 2

Thermal stability of Complex 2 was evaluated by measuring Tg (glass transition temperature) and Tm (melting point) of Complex 1. Tg and Tm were measured by performing thermal analysis (N2 atmosphere, temperature sections: room temperature to 600° C. (10° C./min)-TGA, and from room temperature to 400° C.-DSC, Pan Type: Pt Pan in disposable Al Pan(TGA), and disposable Al pan(DSC)) using thermo gravimetric analysis (TGA) and differential scanning calorimetry (DSC). TGA data of Complex 2 is shown in FIG. 6.

Figure 8:
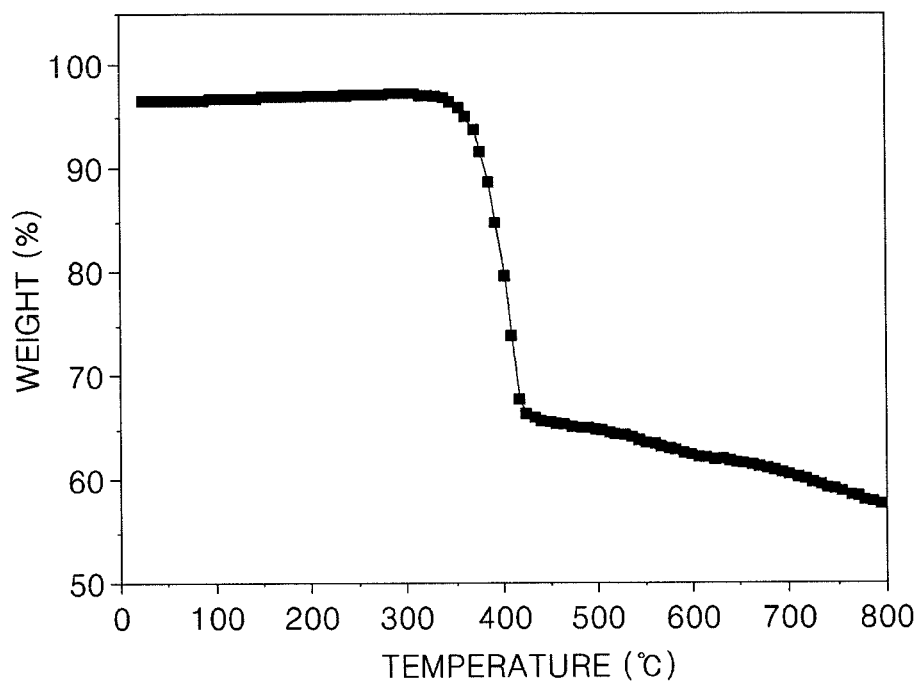
FIG. 8 shows TGA data of complex 2.

From FIG. 8, it was confirmed that Complex 2 has excellent thermal stability.

Evaluation Example 6

Electric Characteristics of Complex 2

Electric characteristics of Complex 2 were identified by evaluating electric characteristics using cyclic voltammetry (CV) (electrolyte: 0.1M $Bu_4NClO_4$/solvent: $CH_2Cl_2$/electrode: 3 electrode system (working electrode: GC, reference electrode: Ag/AgCl, and an auxiliary electrode: Pt)), and results thereof are shown in FIG. 9.

Figure 9:
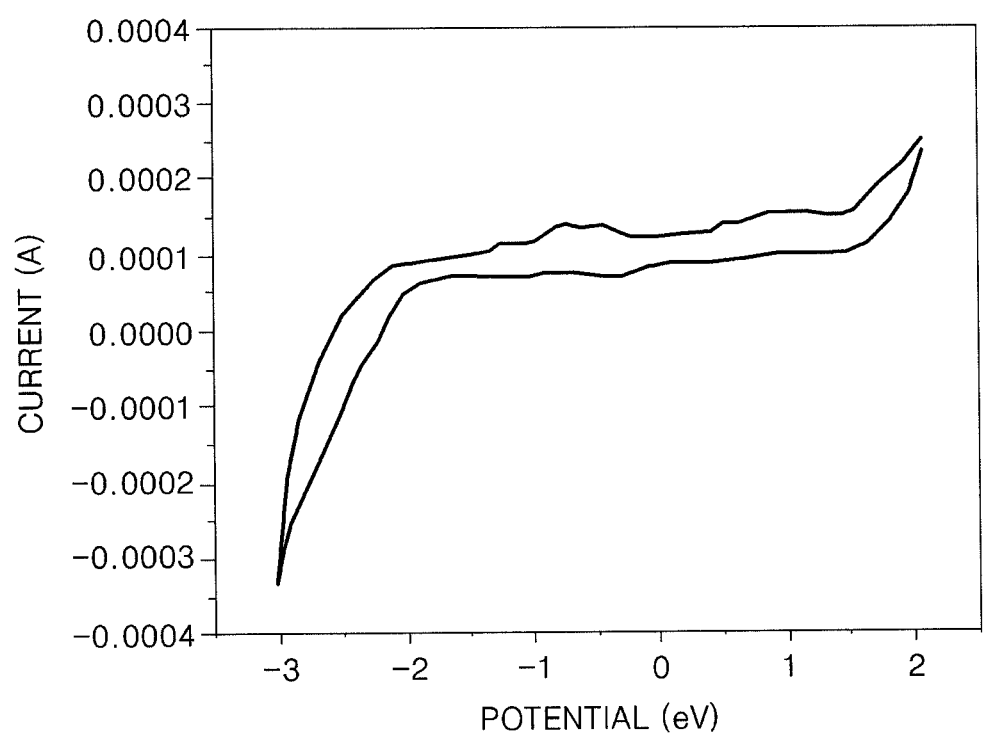
FIG. 9 shows CV data of complex 2.

From FIG. 9, it was confirmed that Complex 2 has an electric characteristics suitable for use as a compound for an organic light-emitting diode.

Example 1

An anode was prepared by cutting a Corning 15 Ωcm² (1200 Å) ITO glass substrate to a size of 50 mm×50 mm×0.7 mm, ultrasonically cleaning the glass substrate using isopropyl alcohol and pure water for 5 minutes each, and then irradiating UV light for 30 minutes and exposing to ozone to clean. Then, the glass substrate was loaded into a vacuum deposition apparatus.

PEDOT:PSS was spin coated on the ITO layer and then heat treated at a temperature of 150° C. to form a hole injection layer having a thickness of 40 nm. PVK (Mw was 25,000), mCP, OXD-7, and Complex 1 were mixed at a weight ratio of 40:27:25:8 (wherein PVK, mCP, and OXD-7 act as a host, and Complex 1 acts as a dopant) and the mixture was spin coated on the hole injection layer and then heat treated at a temperature of 80° C. to form an emission layer having a thickness of 40 nm. Bphen was deposited on the emission layer to form an electron transport layer having a thickness of 20 nm, and LiF was deposited on the electron transport layer to form an electron injection layer having a thickness of 10 Å, and Al was deposited on the electron injection layer to form a second electrode (cathode) having a thickness of 3000 Å, thereby completing the manufacturing of an organic light-emitting diode.

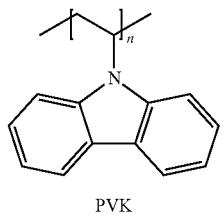

PVK

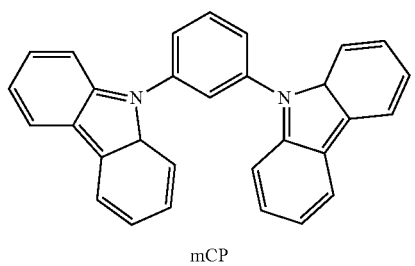

mCP

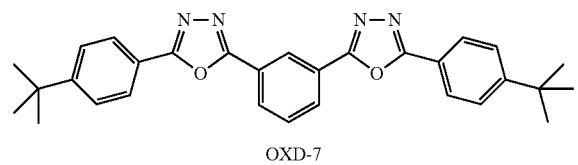

OXD-7

Example 2

An organic light-emitting diode was manufactured in the same manner as in Example 1, except that Complex 2 was used instead of Complex 1 in forming the emission layer.

Example 3

An anode was prepared by cutting a Corning 15 Ωcm² (1200 Å) ITO glass substrate to a size of 50 mm×50 mm×0.7 mm, ultrasonically cleaning the glass substrate using isopropyl alcohol and pure water for 5 minutes each, and then irradiating UV light for 30 minutes and exposing to ozone to clean. Then, the glass substrate was loaded into a vacuum deposition apparatus.

2-TNATA was deposited on the ITO layer to form a hole injection layer having a thickness of 600 Å, and then, NPB was deposited on the hole injection layer to form an hole transport layer having a thickness of 300 Å. Subsequently, CBP(host) and Complex 1(dopant) were co-deposited at a weight ratio of 98:2 on the hole transport layer to form an emission layer having a thickness of 400 Å, and then, Compound 101 was deposited on the emission layer to form an electron transport layer having a thickness of 300 Å. LiF was deposited on the electron transport layer to form an electron injection layer having a thickness of 10 Å, and Al was deposited on the electron injection layer to form a second electrode (cathode) having a thickness of 3000 Å, thereby completing the manufacturing of an organic light-emitting diode.

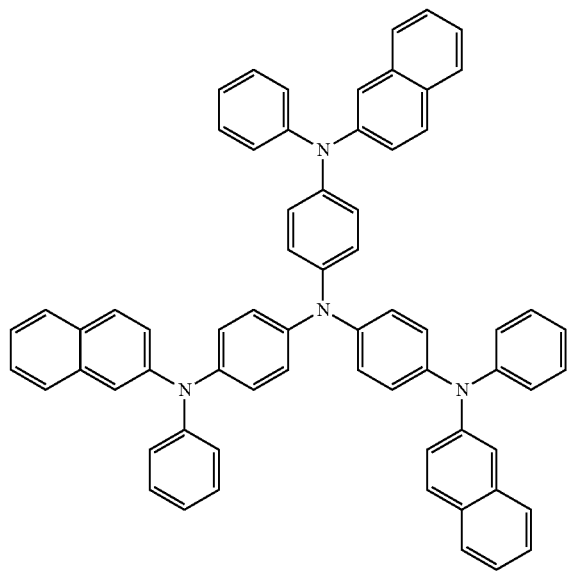

2-TNATA

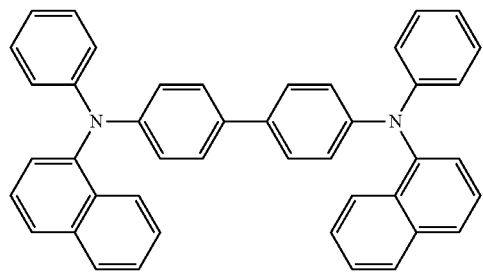

NPB

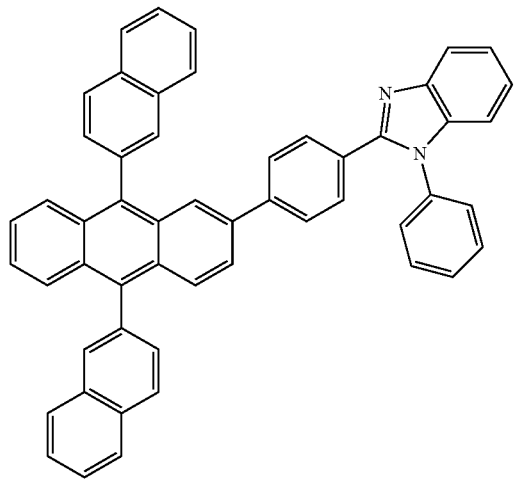

Compound 101

Example 4

An organic light-emitting diode was manufactured in the same manner as in Example 3, except that Complex 2 was used instead of Complex 1 in forming the emission layer.

Comparative Example 1

An organic light-emitting diode was manufactured in the same manner as in Example 3, except that Complex A was used instead of Complex 1 in forming the emission layer.

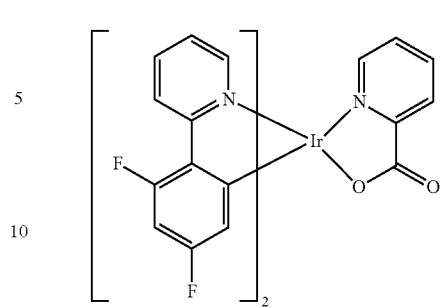

<Complex A>

Comparative Example 2

An organic light-emitting diode was manufactured in the same manner as in Example 3, except that Complex B(Ir(ppy)$_3$) was used instead of Complex 1 in forming the emission layer.

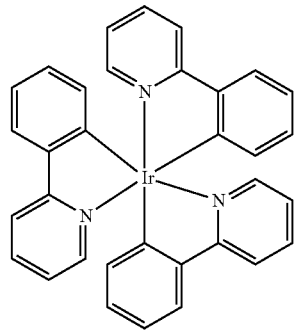

<Complex B>

Ir(ppy)3

Comparative Example 3

An organic light-emitting diode was manufactured in the same manner as in Example 3, except that Complex C was used instead of Complex 1 in forming the emission layer.

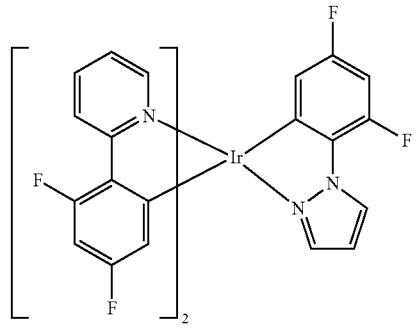

<Complex C>

An organic light-emitting diode was manufactured in the same manner as in Example 3, except that Complex D was used instead of Complex 1 in forming the emission layer.

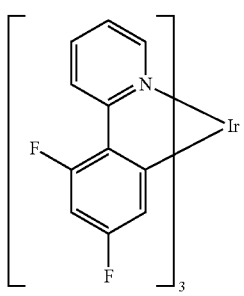

<Complex D>

Comparative Example 5

An organic light-emitting diode was manufactured in the same manner as in Example 3, except that Complex E was used instead of Complex 1 in forming the emission layer.

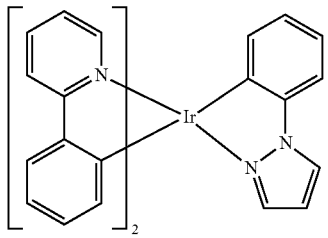

<Complex E>

Efficiency and color purity of the organic light-emitting diodes of Examples 1 to 4 and Comparative Examples 1 and 5 were evaluated by using PR650Spectroscan Source Measurement Unit. (a product of PhotoResearch). Results thereof are shown in Table 1 below.

TABLE 1

|  | Dopant | Efficiency (cd/A) at 10 mA/m² | Color coordinate rate |
|---|---|---|---|
| Example 1 | Complex 1 | 14.6 | 0.24, 0.58 |
| Example 2 | Complex 2 | 15.5 | 0.25, 0.58 |
| Example 3 | Complex 1 | 39.4 | 0.33, 0.62 |
| Example 4 | Complex 2 | 63.7 | 0.27, 0.68 |
| Comp. Ex. 1 | Complex A | 22.5 | 0.17, 0.35 |
| Comp. Ex. 2 | Complex B | 32.4 | 0.28, 0.50 |
| Comp. Ex. 3 | Complex C | 15 | 0.16, 0.30 |
| Comp. Ex. 4 | Complex D | 17.4 | 0.17, 0.34 |
| Comp. Ex. 5 | Complex E | 20.5 | 0.22, 0.55 |

Referring to Table 1, it is confirmed that the organic light-emitting diodes of Examples 1 to 4 had better efficiency and color purities than the organic light-emitting diodes of Comparative Examples 1 to 5.

By way of summation and review, a typical OLED may have a structure including a substrate, and an anode, a hole transport layer (HTL), an emission layer (EML), an electron transport layer (ETL), and a cathode which are sequentially stacked on the substrate. The HTL, the EML, and the ETL may be organic thin films formed of organic compounds.

An operating principle of an OLED having the above-described structure may be as follows. When a voltage is applied between the anode and the cathode, holes injected from the anode move to the EML via the HTL, and electrons injected from the cathode move to the EML via the ETL. The holes and electrons (carriers) recombine in the organic EML to generate excitons. When the excitons drop from an excited state to a ground state, light is emitted.

The organometallic complex according to the embodiments may include a first fluorine and a second fluorine, and accordingly, an electron density of a benzene ring combined with the first fluorine and the second fluorine (which are electron withdrawing groups), may decrease. As a result, light emitted by the organometallic complex may be light that is shifted toward a shorter wavelength region, that is, a blue region. Also, a ligand of the organometallic complex may easily trap electrons, and many excited excitons may be formed together with holes injected into an emission layer. Thus, an organic light-emitting diode including the organometallic complex may have high luminescent efficiency.

While example embodiments have been particularly shown and described above, it will be understood by those of ordinary skill in the art that various changes in form and details may be made therein without departing from the spirit and scope of the present invention as defined by the following claims.

What is claimed is:

1. An organometallic complex, represented by Formula 3A or 3B:

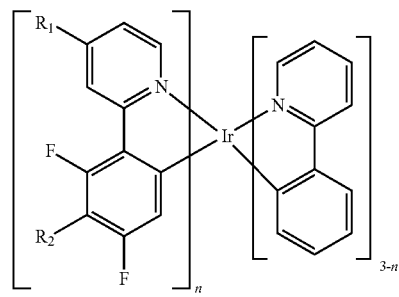

<Formula 3A>

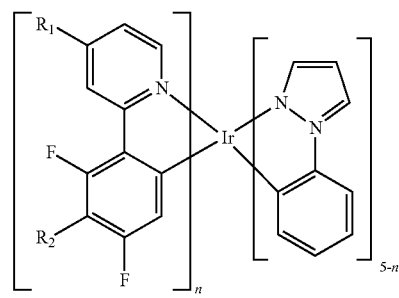

<Formula 3B> wherein, in Formulae 3A and 3B:

$R_1$ is selected from a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an iso-decanyl group, a sec-decanyl group, a tert-decanyl group, and —N($Q_1$)($Q_2$);

$R_2$ is selected from:

a hydrogen atom, F, Cl, a cyano group, a nitro group;

a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl group, an isodecanyl group, a sec-decanyl group, and a tert-decanyl group, each substituted with at least one F;

a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group, each substituted with at least one F; and

—C(=O)(Q$_3$);

wherein Q$_1$ to Q$_3$ are each independently selected from a methyl group, an ethyl group, a propyl group, a n-butyl group, an isobutyl group, a sec-butyl group, a tert-butyl group, a n-pentyl group, an isopentyl group, a sec-pentyl group, a tert-pentyl group, a n-hexyl group, an isohexyl group, a sec-hexyl group, a tert-hexyl group, a n-heptyl group, an isoheptyl group, a sec-heptyl group, a tert-heptyl group, a n-octyl group, an isooctyl group, a sec-octyl group, a tert-octyl group, a n-nonyl group, an isononyl group, a sec-nonyl group, a tert-nonyl group, a n-decanyl, isodecanyl, sec-decanyl and tert-decanyl, each substituted with at least one F; and a phenyl group, a naphthyl group, an anthryl group, a pyrenyl group, a phenanthrenyl group, a fluorenyl group, a pyrimidinyl group, a pyrazinyl group, a pyridazinyl group, a triazinyl group, a quinolinyl group, an isoquinolinyl group, a quinoxalinyl group, a phenanthrolinyl group, and a carbazolyl group, each substituted with at least one selected from F and a C$_1$-C$_{20}$ alkyl group substituted with at least one F; and n is 1 or 2.

2. An organometallic complex, wherein the organometallic complex is at least one selected from Complexes 1 to 16:

1
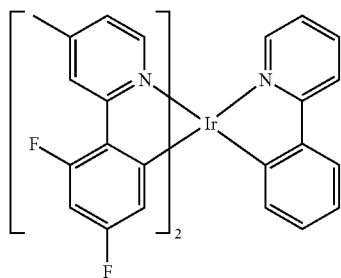

2
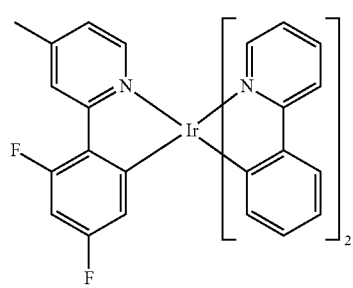

3
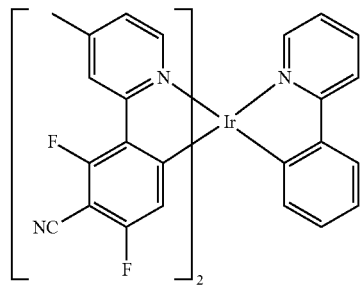

4
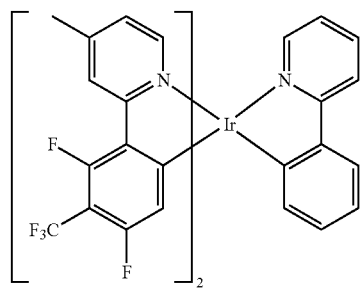

5
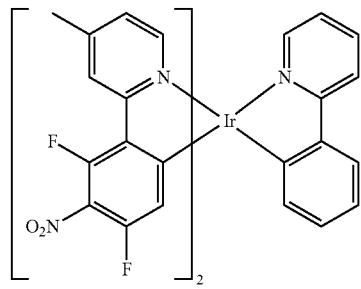

6
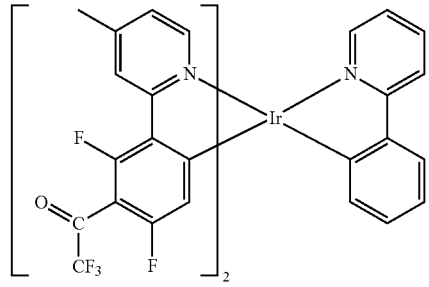

7
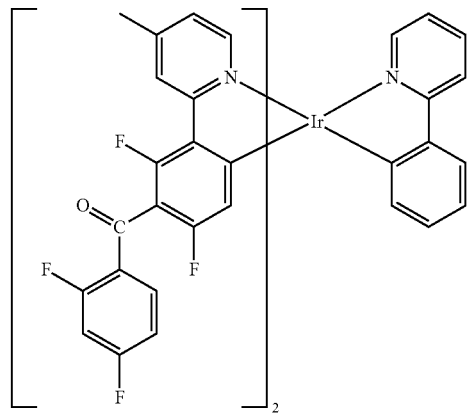

8
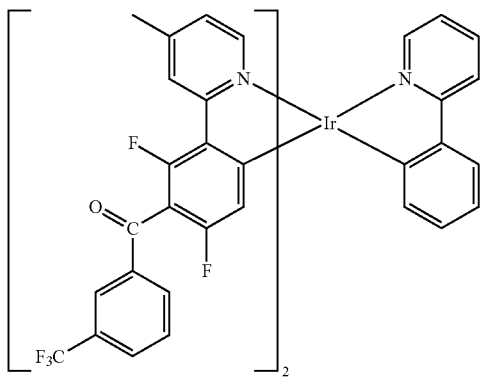
9
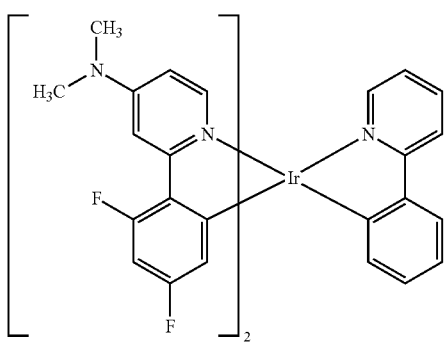
10
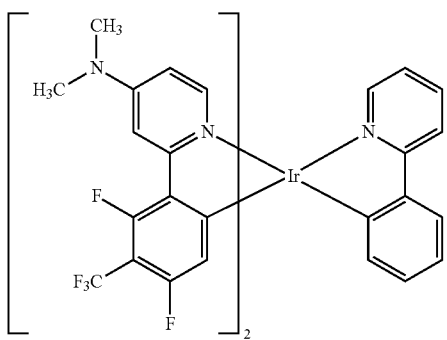
11
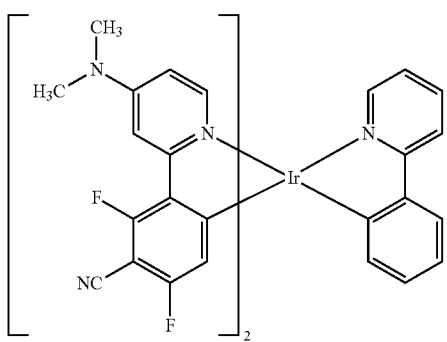
12
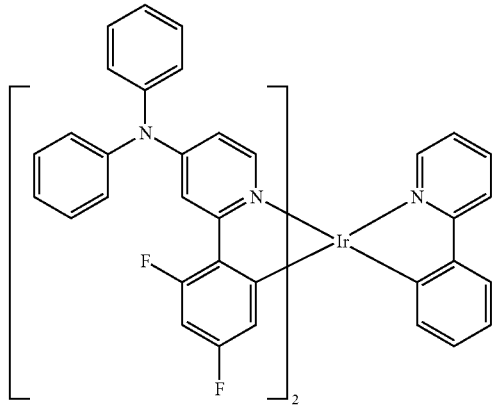
13
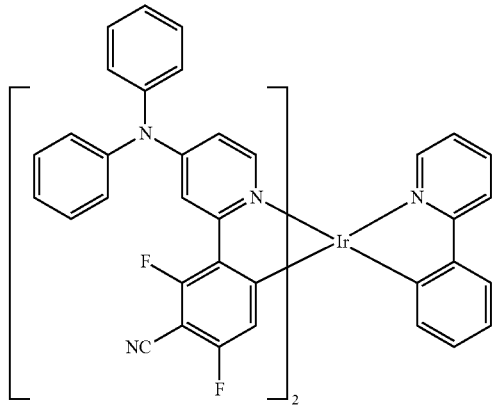
14
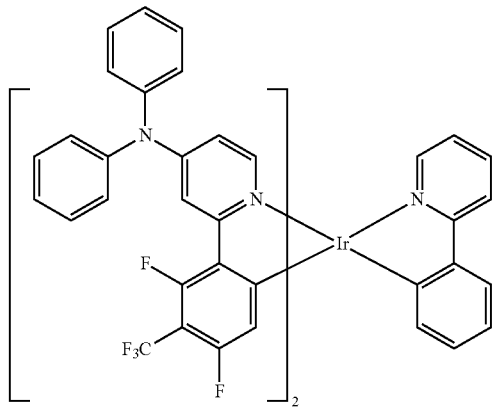
15
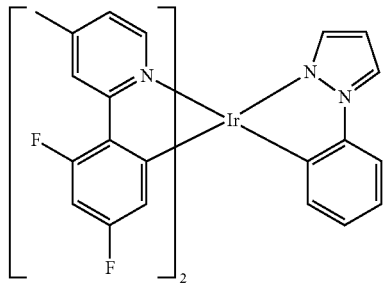

-continued

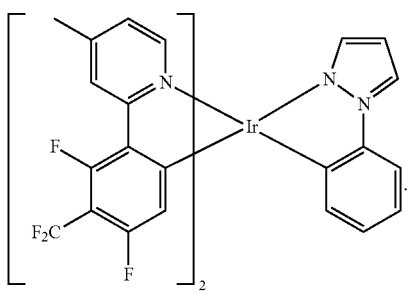

3. An organic light-emitting diode, comprising:
a first electrode;
a second electrode facing the first electrode; and
an organic layer between the first electrode and the second electrode, the organic layer including an emission layer, wherein the organic layer includes one or more of the organometallic complex as claimed in claim 1.

4. The organic light-emitting diode of claim 3, wherein:
the emission layer includes the organometallic complex as a phosphorescent dopant, and
the emission layer further includes a host.

5. The organic light-emitting diode of claim 4, wherein:
a concentration of the organometallic complex in the emission layer is in a range of about 0.01 wt % to about 15 wt % based on 100 wt % of the emission layer.

6. The organic light-emitting diode of claim 3, wherein the organic layer further includes:
between the first electrode and the emission layer, at least one layer selected from a hole injection layer, a hole transport layer, a functional layer having a hole injection function and a hole transportation function, a buffer layer, and an electron blocking layer, and
between the emission layer and the second electrode, at least one layer selected from a hole blocking layer, an electron transport layer, and an electron injection layer.

7. The organic light-emitting diode of claim 6, wherein:
an electron transport layer is between the emission layer and the second electrode, and
the electron transport layer includes an electron transportation organic compound and a metal-containing material.

* * * * *